(12) United States Patent
Apple

(10) Patent No.: US 10,188,292 B2
(45) Date of Patent: *Jan. 29, 2019

(54) DEVICE FOR SCREENING CONVERGENCE INSUFFICIENCY AND RELATED COMPUTER IMPLEMENTED METHODS

(71) Applicant: Howard P. Apple, Winter Park, FL (US)

(72) Inventor: Howard P. Apple, Winter Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/697,880

(22) Filed: Sep. 7, 2017

(65) Prior Publication Data

US 2018/0064329 A1 Mar. 8, 2018

Related U.S. Application Data

(60) Provisional application No. 62/385,136, filed on Sep. 8, 2016.

(51) Int. Cl.
*A61B 3/113* (2006.01)
*A61B 3/08* (2006.01)
(Continued)

(52) U.S. Cl.
CPC .......... *A61B 3/113* (2013.01); *A61B 3/0041* (2013.01); *A61B 3/0058* (2013.01);
(Continued)

(58) Field of Classification Search
CPC ........... A61B 3/0058; A61B 3/08; A61B 3/09;
A61B 3/18; A61B 3/113; A61B 3/0025; A61B 3/0041; A61B 3/0091; A61B 3/111; A61B 3/145; G06T 7/292; G06T 2207/30041
See application file for complete search history.

(56) References Cited

U.S. PATENT DOCUMENTS 5,026,151 A 6/1991 Waltuck et al.
5,355,895 A 10/1994 Hay
(Continued)

FOREIGN PATENT DOCUMENTS

CN 103393398 11/2013
EP 2891953 7/2015
(Continued)

*Primary Examiner* — Jordan Schwartz
(74) *Attorney, Agent, or Firm* — Allen, Dyer, Doppelt + Gilchrist, PA

(57) ABSTRACT

A device is for screening a person for CI and may include a binocular viewer, a display adjacent the binocular viewer, and a processor and associated memory cooperating with the display. The processor may be configured to display on the display a first visual stimulus and a second visual stimulus, cause, in alternating fashion, convergent movement and divergent movement in the first visual stimulus and the second visual stimulus along a visual stimulus path, determine respective centroid positions of the second eye and the first eye during the convergent and divergent movement of the first visual stimulus and the second visual stimulus, and calculate an IPD, and compare the IPD with the visual stimulus path to obtain a dynamic IPD, the dynamic IPD serving as an indicator for whether the person has CI.

20 Claims, 21 Drawing Sheets

(51) Int. Cl.

| | | |
|---|---|---|
| *A61B 3/11* | (2006.01) | |
| *G06T 7/246* | (2017.01) | |
| *A61B 3/14* | (2006.01) | |
| *A61B 5/11* | (2006.01) | |
| *G06T 7/00* | (2017.01) | |
| *G06T 7/292* | (2017.01) | |
| *G06T 7/73* | (2017.01) | |
| *A61B 3/18* | (2006.01) | |
| *G06T 11/20* | (2006.01) | |
| *G06T 11/60* | (2006.01) | |
| *A61B 3/09* | (2006.01) | |
| *A61B 3/00* | (2006.01) | |

(52) U.S. Cl.
CPC .............. *A61B 3/0091* (2013.01); *A61B 3/08* (2013.01); *A61B 3/09* (2013.01); *A61B 3/111* (2013.01); *A61B 3/14* (2013.01); *A61B 3/145* (2013.01); *A61B 3/18* (2013.01); *A61B 5/1103* (2013.01); *G06T 7/0012* (2013.01); *G06T 7/0016* (2013.01); *G06T 7/246* (2017.01); *G06T 7/292* (2017.01); *G06T 7/74* (2017.01); *G06T 11/206* (2013.01); *G06T 11/60* (2013.01); *A61B 3/0025* (2013.01); *A61B 2560/0475* (2013.01); *G06T 2207/10016* (2013.01); *G06T 2207/10048* (2013.01); *G06T 2207/20024* (2013.01); *G06T 2207/30041* (2013.01)

(56) References Cited

U.S. PATENT DOCUMENTS

| | | | |
|---|---|---|---|
| 5,825,458 A | | 10/1998 | Cooper |
| 5,953,102 A | | 9/1999 | Berry |
| 6,325,513 B1 | | 12/2001 | Bergner et al. |
| 6,545,650 B1 | | 4/2003 | Yamada et al. |
| 7,309,125 B2 | | 12/2007 | Pugach et al. |
| 7,367,675 B2 | | 5/2008 | Maddalena et al. |
| 8,016,420 B2 | | 9/2011 | Yee et al. |
| 8,668,334 B2 | | 3/2014 | Krenik |
| 9,504,380 B1 | * | 11/2016 | Quaid .................... A61B 3/085 |
| 2003/0211449 A1 | * | 11/2003 | Seiller ................ G09B 19/0038 434/258 |
| 2006/0087618 A1 | | 4/2006 | Smart et al. |
| 2007/0013868 A1 | | 1/2007 | Pugach et al. |
| 2007/0200927 A1 | | 8/2007 | Krenik |
| 2008/0212032 A1 | | 9/2008 | Seiller et al. |
| 2008/0284979 A1 | | 11/2008 | Yee et al. |
| 2010/0324454 A1 | | 12/2010 | Kircher et al. |
| 2011/0157550 A1 | | 6/2011 | Chen et al. |
| 2012/0105609 A1 | * | 5/2012 | Qi ........................... A61B 3/08 348/54 |
| 2012/0221075 A1 | | 8/2012 | Bentwich |
| 2012/0229768 A1 | | 9/2012 | Gramatikov et al. |
| 2012/0253770 A1 | | 10/2012 | Stern et al. |
| 2012/0307203 A1 | | 12/2012 | Vendel et al. |
| 2013/0044291 A1 | * | 2/2013 | Kato .................... A61B 3/0025 351/209 |
| 2014/0362346 A1 | | 12/2014 | Leinonen et al. |
| 2015/0320306 A1 | | 11/2015 | Voigtmann et al. |
| 2016/0106315 A1 | | 4/2016 | Kempinski |
| 2016/0262608 A1 | | 9/2016 | Krueger |
| 2017/0290504 A1 | * | 10/2017 | Khaderi ................ A63F 13/212 |

FOREIGN PATENT DOCUMENTS

| | | |
|---|---|---|
| JP | 2002017677 | 1/2002 |
| WO | WO2008120635 | 10/2008 |
| WO | WO 2016/020229 | 2/2016 |

\* cited by examiner

STIMULI UNMERGED TO SUBJECT'S EYES

STIMULI MERGING TO SUBJECT'S EYES

STIMULI MERGED TO SUBJECT'S EYES

THRESHOLD
EYE IMAGE

CLEARED BORDER
DELETED SMALL BLOBS 136.2396    192.6549

ONE BLOB
REMAINING

DEVICE FOR SCREENING CONVERGENCE INSUFFICIENCY AND RELATED COMPUTER IMPLEMENTED METHODS

RELATED APPLICATION

This application is based upon prior filed Application No. 62/385,136 filed Sep. 8, 2016, the entire subject matter of which is incorporated herein by reference in its entirety.

TECHNICAL FIELD

This present application relates to a medical device, and more particularly, to a device for screening visual issues in a patient.

BACKGROUND

Convergence Insufficiency (CI) occurs when a subject's brain fails to coordinate images from both eyes while trying to focus on a nearby object. When a subject reads or looks at a close object, the subject's eyes must both turn inwardly (convergence) to focus. In studies that used standardized definitions of Convergence Insufficiency, investigators have reported a prevalence of 4.2% to 6% in school and clinic settings. Convergence Insufficiency is a common binocular vision disorder that is often associated with a variety of symptoms, including eyestrain, headaches, blurred vision, diplopia (double vision), sleepiness, difficulty concentrating, movement of print while reading, and loss of comprehension after short periods of reading or performing close activities.

Also, CI can cause difficulty with reading. This may make parents or teachers suspect that a child has a learning disability, instead of an eye disorder. In the past, CI disorder has often gone undetected because CI testing is not included in (1) a pediatrician's eye test; (2) school screenings; or (3) basic eye exams. A person can pass the 20/20 eye chart test and still have CI.

Currently, there is no consensus on norms for existing clinical methods for detecting CI or whether these are the only clinical measures required. Multiple subjective and objective decisions, including estimates of distance and time, are required by both the subject and the clinician. Objective measurements rely on examiner expertise and may be difficult for beginners to observe. Subjective measurements require patient cooperation to attain reliable results. In summary, present clinical methods have significant problems regarding accuracy and reproducibility, because they require subjective feedback from the subject, and because of clinician variability.

SUMMARY

Generally, a device is for screening a person for CI. The device may include a binocular viewer comprising a first eyepiece to receive a first eye of the person, a second eyepiece to receive a second eye of the person, a first image sensor adjacent the first eyepiece, and a second image sensor adjacent the second eyepiece, a display adjacent the binocular viewer, and a processor and associated memory cooperating with the display. The processor may be configured to record, with the first image sensor, movement of the first eye, record, with the second image sensor, movement of the second eye, and display on the display a first visual stimulus and a second visual stimulus. The processor may be configured to cause, in alternating fashion, convergent movement and divergent movement in the first visual stimulus and the second visual stimulus along a visual stimulus path, determine respective centroid positions of the second eye and the first eye during the convergent and divergent movement of the first visual stimulus and the second visual stimulus, and calculate an interpupillary distance (IPD), and compare the IPD with the visual stimulus path to obtain a dynamic IPD, the dynamic IPD serving as an indicator for whether the person has CI.

In some embodiments, a duration of each of the convergent movement and the divergent movement is 80-100 seconds. The device may also include a first infrared (IR) source configured to irradiate the first eye and a second IR illuminator configured to irradiate second eye, and the processor and memory may be configured to generate a first plurality of video frames showing movement of the first eye, and generate a second plurality of video frames showing movement of the second eye.

More specifically, the processor and memory may be configured to identify second blink pixels comprising second eye blinks in the second plurality of video frames, and form a third plurality of video frames by removing the second blink pixels from the second plurality of video frames. The processor and memory may be configured to identify first blink pixels comprising first eye blinks in the first plurality of video frames, and form a fourth plurality of video frames by removing the first blink pixels from the first plurality of video frames.

Also, the processor and memory may be configured to generate the first plurality of video frames by performing at least filtering each of the first plurality of video frames using a pixel intensity threshold to form a third plurality of video frames, each of the third plurality of video frames comprising a black background in combination with a white background, a first eye image, the third plurality of video frames comprising an N number of video frames, and filtering each of the second plurality of video frames using the pixel intensity threshold to form a fourth plurality of video frames, each of the fourth plurality of video frames comprising a black background in combination with a white background, a second eye image, the fourth plurality of video frames comprising an M number of video frames. The processor and memory may be configured to generate the first plurality of video frames by performing at least determining, for each of the third plurality of video frames, x and y coordinates for a first eye pupil centroid, and generating a first plurality of x coordinate datasets. An ith x coordinate dataset represents a location of an ith second pupil centroid, and i is greater than or equal to 1 and less than or equal to N. The processor and memory may be configured to generate the first plurality of video frames by performing at least determining, for each of the fourth plurality of video frames, x and y coordinates for a second eye pupil centroid, and generating a second plurality of x coordinate datasets. A jth x coordinate dataset represents a location of a jth first pupilar centroid, and j is greater than or equal to 1 and less than or equal to M.

The processor and memory may be configured to graphically display a first curve comprising N x coordinate datasets versus time, and graphically display a second curve comprising M x coordinate datasets versus time. The processor and memory may also be configured to set $i=1$ and $j=1$, subtract the ith x coordinate dataset from the jth x coordinate dataset to form a kth x coordinate dataset, each of the kth x coordinate dataset representing a hth dynamic IPD, when i is less than N, set $i=i+1$, when j is less than M, set $j=j+1$, and repeat the setting and the subtracting until at least one of $i=N$ and $j=M$ is true.

The processor and memory may be configured to form a third curve comprising each of the hth dynamic IPD versus time. The processor and memory may be configured to identify a first substantially linear portion of the third curve, the first substantially linear portion comprising a positive slope, identify a second substantially linear portion of the third curve, the second substantially linear portion comprising a negative slope, generate a graphical plot of the visual stimulus path, the graphical plot comprising a first linear portion comprising a positive slope and a second linear portion comprising a negative slope, overlap the third curve onto the graphical plot of the visual stimulus path, and adjust the third curve to fit onto graphical plot of the visual stimulus path. The processor and memory may be configured to compare the dynamic IPD with the visual stimulus path by performing at least optimizing a graph of dynamic IPDs with at least one parameter, and merging the optimized graph of dynamic IPDs with the visual stimulus path.

Another aspect is directed to a method for screening a person for CI. The method may include recording, with a first image sensor, movement of a first eye of the person, recording, with a second image sensor, movement of a second eye of the person, and displaying on a display a first visual stimulus and a second visual stimulus. The method may include causing, in alternating fashion, convergent movement and divergent movement in the first visual stimulus and the second visual stimulus along a visual stimulus path, determining respective centroid positions of the second eye and the first eye during the convergent and divergent movement of the first visual stimulus and the second visual stimulus, and using a processor and memory associated with the display, and the first and second image sensors for calculating an interpupillary distance (IPD), and comparing the IPD with the visual stimulus path to obtain a dynamic IPD, the dynamic IPD serving as an indicator for whether the person has CI.

Another aspect is directed to a device for screening a person for CI with a binocular viewer comprising a first eyepiece to receive a first eye of the person, a second eyepiece to receive a second eye of the person, a first image sensor adjacent the first eyepiece, and a second image sensor adjacent the second eyepiece. The device may include a display adjacent the binocular viewer, and a processor and associated memory cooperating with the display. The processor may be configured to record, with the first image sensor, movement of the first eye, record, with the second image sensor, movement of the second eye, and display on the display a first visual stimulus and a second visual stimulus. The processor may be configured to cause, in alternating fashion, convergent movement and divergent movement in the first visual stimulus and the second visual stimulus along a visual stimulus path, determine respective centroid positions of the second eye and the first eye during the convergent and divergent movement of the first visual stimulus and the second visual stimulus, and calculate an interpupillary distance (IPD), and compare the IPD with the visual stimulus path to obtain a dynamic IPD, the dynamic IPD serving as an indicator for whether the person has CI.

Another aspect is directed to a non-transitory computer-readable medium having computer-executable instructions for causing a computing device comprising a processor and associated memory to perform a method for screening a person for CI. The method may include recording, with a first image sensor, movement of a first eye of the person, recording, with a second image sensor, movement of a second eye of the person, and displaying on a display a first visual stimulus and a second visual stimulus. The method may include causing, in alternating fashion, convergent movement and divergent movement in the first visual stimulus and the second visual stimulus along a visual stimulus path, determining respective centroid positions of the second eye and the first eye during the convergent and divergent movement of the first visual stimulus and the second visual stimulus, and calculating an IPD, and comparing the IPD with the visual stimulus path to obtain a dynamic IPD, the dynamic IPD serving as an indicator for whether the person has CI.

DETAILED DESCRIPTION

Figure 1:
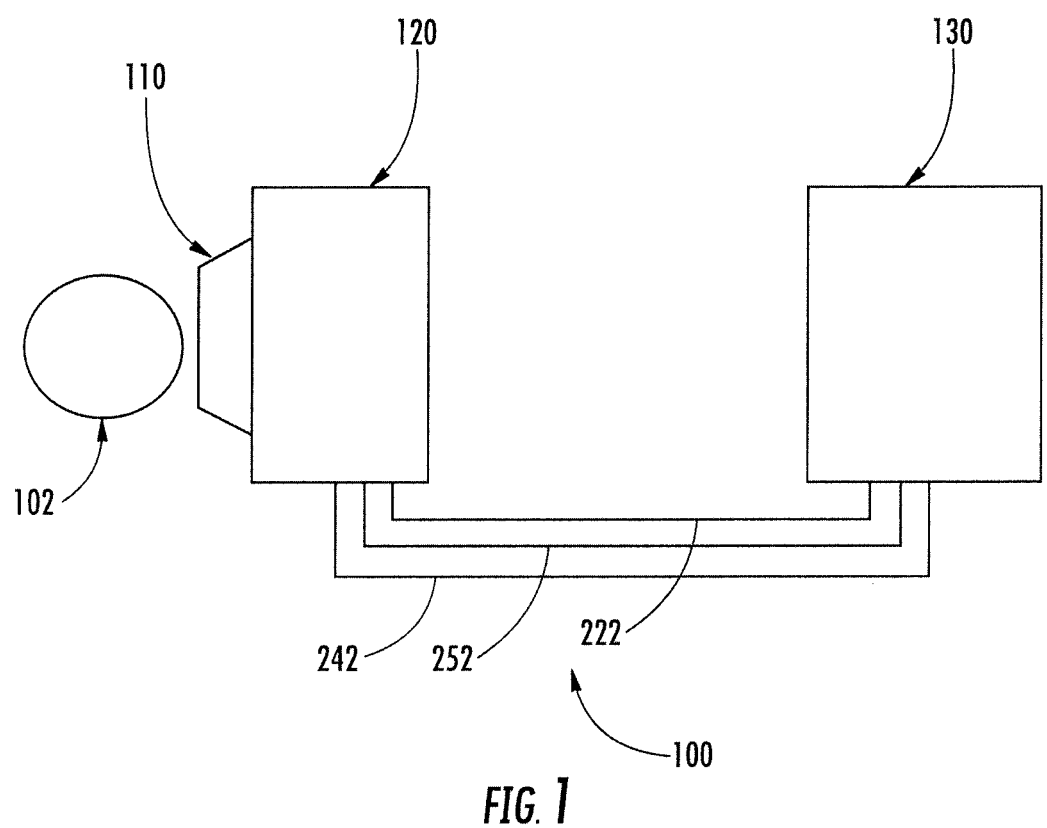
FIG. 1 is a schematic diagram of an apparatus to screen for CI, according to the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout.

Certain embodiments of Applicant's disclosure recite a method to screen a person for CI. The steps of the method comprise providing a screening apparatus, positioning a patient in front of the screening apparatus so that the patient looks into the apparatus, displaying visual stimuli convergently and divergently to generate a visual stimulus path, determining respective centroid positions of each eye, calculating an interpupillary distance (IPD) between the eyes, and comparing the IPD with the visual stimulus path to obtain a dynamic IPD, which is an indicator for whether the patient has CI.

Further, certain embodiments of Applicant's disclosure describe the screening apparatus with a binocular viewer and a housing attached to the binocular viewer. Further, the binocular viewer comprises two eyepieces, two mirrors, and two infrared (IR) illuminators; and the housing comprises two video cameras and a visual display device. In certain embodiments, the visual display is movable.

In certain embodiments, the binocular viewer comprises two eyepieces and two mirrors. The binocular viewer does not contain any (IR) illuminators. In other embodiments, the binocular viewer comprises two eyepieces, four mirrors, and two infrared (IR) illuminators. In yet some other embodiments, the binocular viewer comprises two eyepieces and four mirrors, without the IR illuminators. In addition, in certain embodiments, the visual display is movable.

The Applicant's disclosure is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

As a general matter when viewing an object, humans and many other animals enjoy stereoscopic vision. Because the two eyes are separated horizontally, the images perceived in the two eyes are slightly different and the difference is proportional to the relative depth. The visual areas in the brain measure these differences, and "merge" the two different objects into a single object. In overview, Applicant's apparatus and method provide a mechanism to evaluate the ability of the subject's brain to merge the two perceived objects into a single 2-D or 3-D image.

Figure 2A:
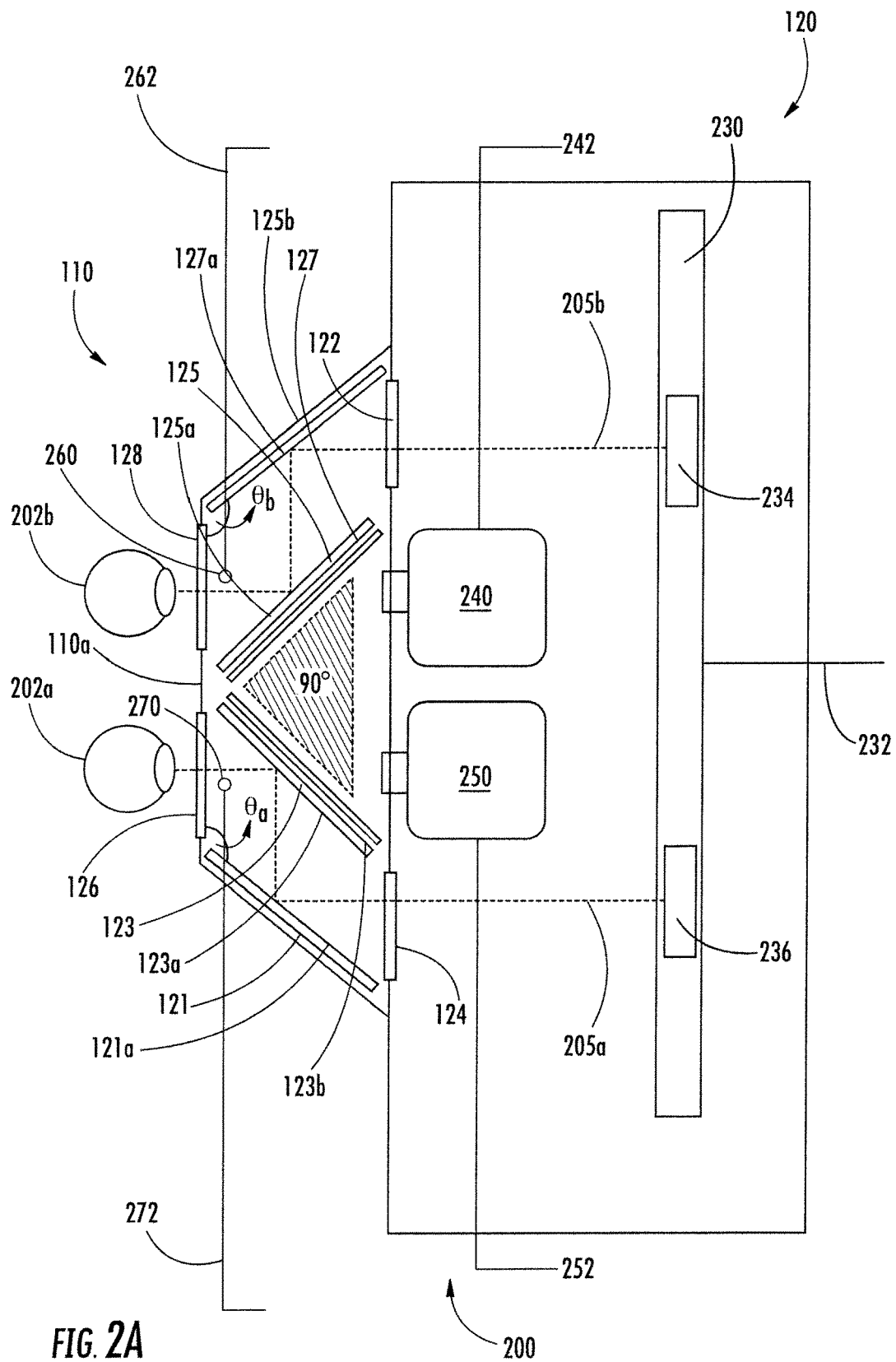
FIG. 2A is a schematic diagram of a binocular viewer 110 and a housing comprising one visual display, according to the present disclosure.
Figure 2B:
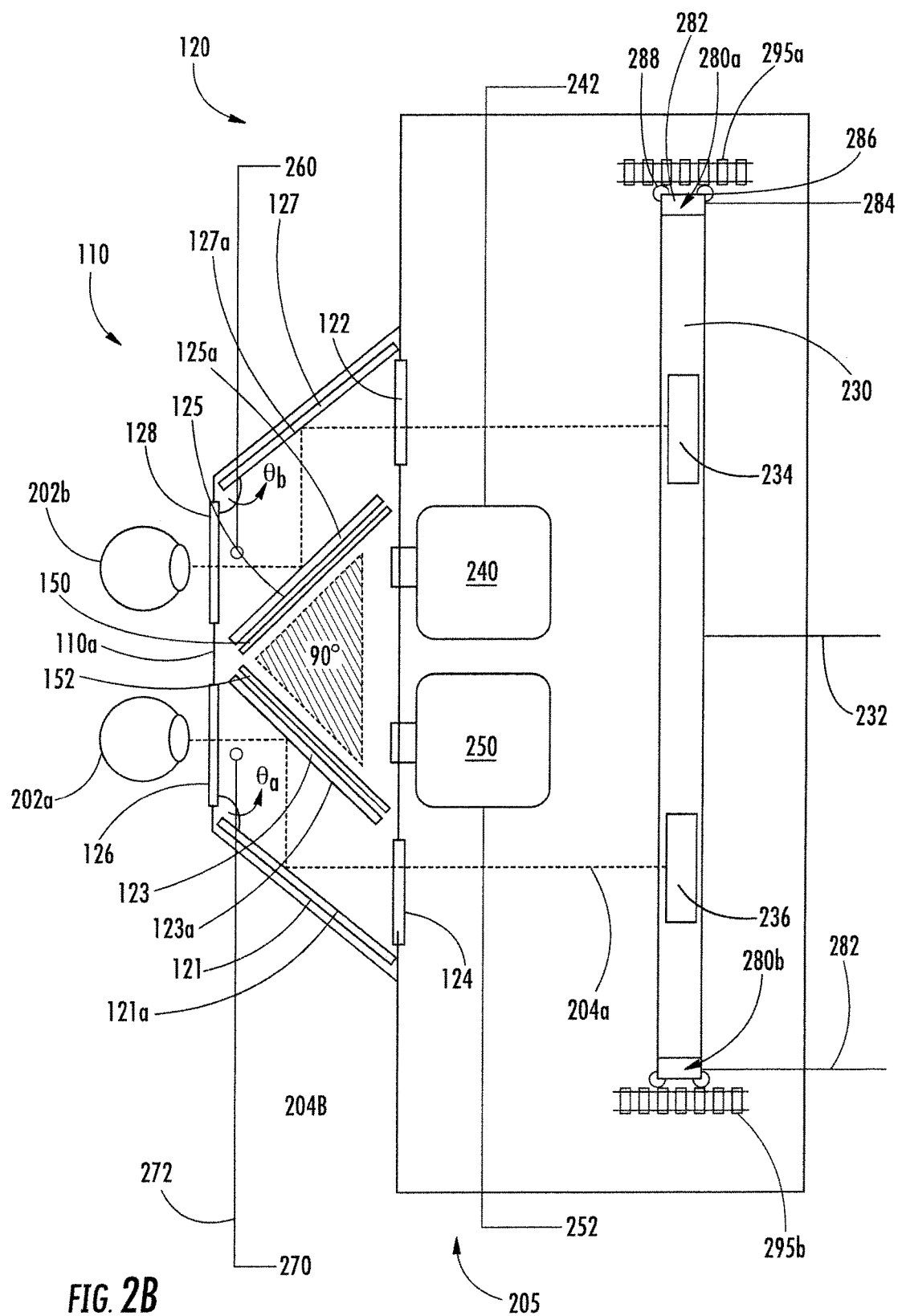
FIG. 2B is a schematic diagram of binocular viewer and the housing comprising one movable visual display, according to the present disclosure.

Referring now to FIG. 1, Applicant's assembly for objectively screening subjects for Convergence Insufficiency comprises a binocular viewer 110, a housing 120 attached to binocular viewer 110, and a controller 130. A subject 102 is positioned in front of binocular viewer 110. Referring now to FIGS. 1, 2A and 2B, the subject 102 positions his or her eyes 202A and 202B in front of eyepieces 126 and 128, respectively. In certain embodiments, the subject 102 places both hands on a surface supporting housing 120 to eliminate head movement during the examination. Further, the distance between the two eyepieces 126 and 128 can be adjusted to match a distance between the test subject's eyes 202A and 202B.

In other embodiments, a virtual reality (VR) mask/headset fits over binocular viewer 110. Applicant has found that the VR mask faceplate can position the test subject's head into the best position for testing and reduce movement.

In certain embodiments, Applicant's apparatus comprises two (2) front surface mirrors and two (2) cold mirrors disposed in housing 120 and a single visual display device. In other embodiments, Applicant's apparatus comprises two (2) front surface mirrors and two (2) cold mirrors disposed in housing 120 and a single visual display device, wherein the visual display device is moveable within the housing.

In yet other embodiments, Applicant's apparatus comprises two (2) front surface mirrors and two (2) cold mirrors disposed in housing 120, a single visual display device, and two (2) infrared emitters disposed in housing 120. In still other embodiments, Applicant's apparatus comprises two (2) different front surface mirrors and two (2) cold mirrors disposed in housing 120, a single visual display device, and two (2) infrared emitters disposed in housing 120, wherein the visual display device is moveable within the housing.

In further embodiments, Applicant's apparatus comprises two (2) cold mirrors disposed in housing 120 and two different visual display devices. In other embodiments, Applicant's apparatus comprises two (2) front surface (or cold) different mirrors disposed in housing 120 and two different visual display devices, wherein one or more of the visual display devices is moveable within the housing. In further embodiments, Applicant's apparatus comprises two (2) different front surface (or cold) mirrors disposed in housing 120, two (2) different visual display devices disposed in housing 120, and two (2) infrared emitters disposed in housing 120. In other embodiments, Applicant's apparatus comprises two (2) different front surface (or cold) mirrors disposed in housing 120, two (2) different visual display devices disposed in housing 120, and two (2) infrared emitters disposed in housing 120, wherein one or more of the visual display devices is moveable within housing 120.

Figure 15:
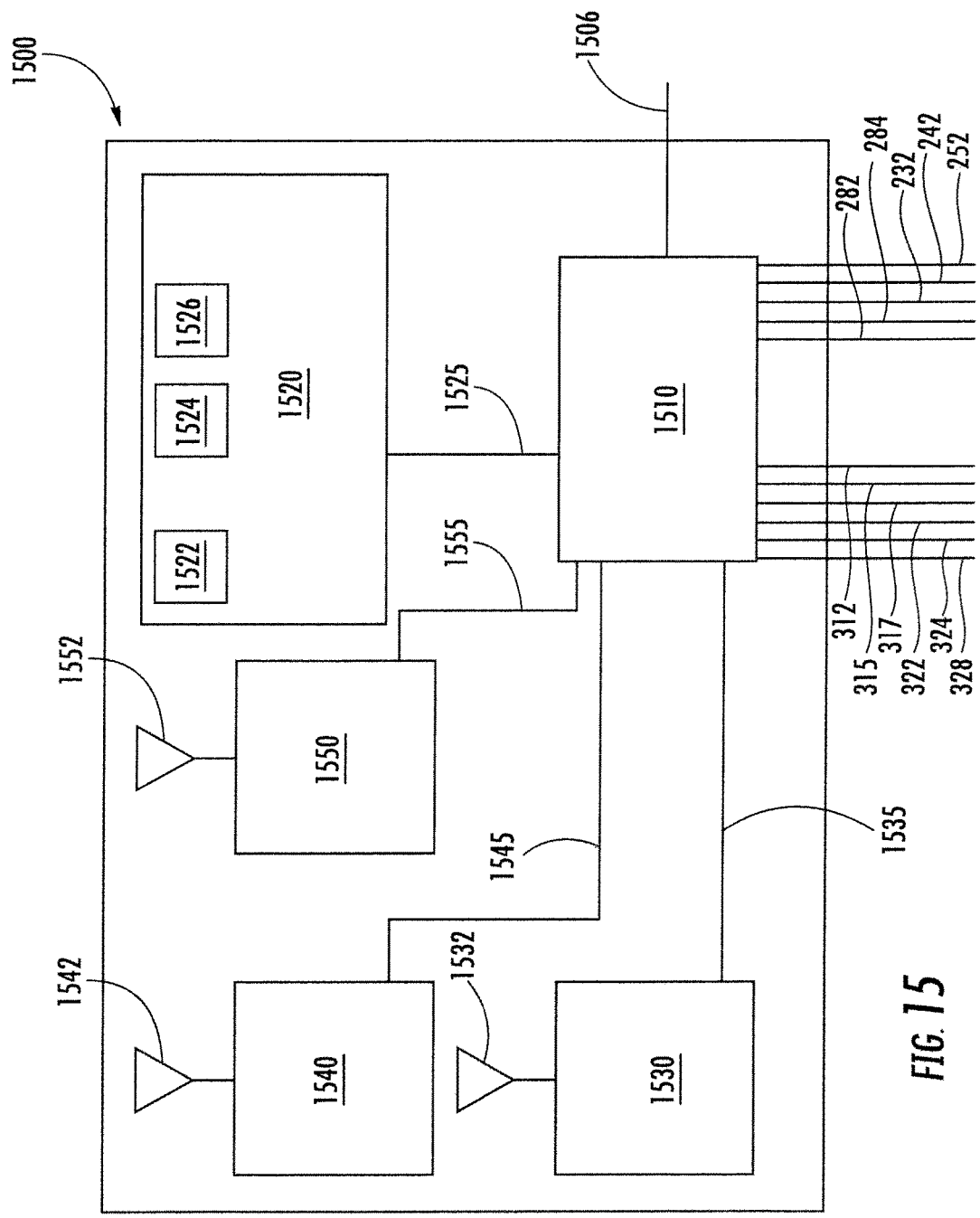
FIG. 15 is a schematic diagram of a controller depicted in FIG. 1.

Referring now to FIGS. 1 and 2A, housing 120 comprises a camera 240, a camera 250, and a visual display 230 (FIG. 2). A controller 130 is in communication with both cameras 240 and 250, and the visual display 230. Referring now to FIG. 15, controller 1500 comprises processor 1510, memory 1520 interconnected with processor 1510 via communication link 1525, optional Bluetooth module 1530 interconnected with processor 1510 via communication link 1535, optional RFID module 1540 interconnected with processor 1510 via communication link 1545, and optional "WI-FI" module 1550 interconnected with processor 1510 via communication link 1555.

In the illustrated embodiment of FIG. 15, microcode 1522, instructions 1524, and database 1526, are encoded in memory 1520. In certain embodiments, memory 1520 comprises non-volatile memory. In certain embodiments, memory 1520 comprises battery backed up RAM, a magnetic hard disk assembly, an optical disk assembly, and/or electronic memory. By "electronic memory," Applicants mean a PROM, EPROM, EEPROM, SMARTMEDIA, FLASHMEDIA, and the like.

Processor 1510 uses microcode 1522 to operate controller 1500. Processor 1510 uses microcode 1522, instructions 1524, and database 1526, to operate Applicant's assembly 100, Bluetooth module 1530, RFID module 1540, and WI-FI module 1550.

In certain embodiments, processor 1510, memory 1520, optional Bluetooth module 1530, optional RFID module 1540, and optional "WI-FI" module 1550, are integrated into an application specific integrated circuit, i.e. an "ASIC."

In the illustrated embodiment of FIG. 2A, the binocular viewer 110 comprises two eyepieces 126 and 128, two infrared (IR) emitters 260 and 270, and four mirrors 121, 123, 125, and 127. The eyepieces 126 and 128 are disposed in surface 110a of binocular viewer 110. Each eye sees a different, moveable stimulus on display 230. In certain embodiments, the stimulus can be white shown on black background. In other embodiments, the stimulus can be black shown on white background.

In certain embodiments, mirrors 123 and 125 are cold mirrors, which allow light to go through on one side but is reflective on the other side, such as sides 123a and 125a are reflective (FIG. 2A, these sides facing subject's eyes); whereas mirrors 121 and 127 are surface mirrors, which reflect normally on one side and the other side is non-reflective to avoid extra light issue. For example, sides 121a and 127a (FIG. 2a) of the surface mirrors reflect normally. Further, the reflective side of a cold mirror can block about 90% of visible light, which has a spectrum up to about 650 nanometers. As described herein, "about" is used to describe a plus or minus 10% difference in any measurements. The non-reflective sides 123b and 125b (FIG. 2A) of mirrors 123 and 125 allow cameras 240 and 250 to be positioned behind mirrors without causing obstruction or distraction to testing subjects because they are looking at the reflective sides 123a and 125a of the mirrors during the test and cannot see the cameras. Further, in some embodiments, an IR filter 150 (FIG. 2B) is disposed parallel to mirror 125 and another IR filter 152 (FIG. 2B) is disposed parallel to mirror 123. The IR filters block light of wavelengths up to about 700 nanometers and they assist in preventing the light from leaking back into the cameras 240 and 250, which will cause blur or glare.

A first eye 202A of a test subject 102 looks through the eyepiece 126 to observe moveable visual stimulus 236 shown on visual display 230. A sight path for first eye 202A passes through eyepiece 126 onto mirror 123, is redirected by reflective surface 123a onto mirror 121, is redirected by reflective surface 121a onto display 230.

A second eye 202B of a test subject 102 looks through the eyepiece 128 to observe moveable visual stimulus 234 shown on visual display 230. A sight path for second eye 202A passes through eyepiece 128 onto mirror 125, is redirected by reflective surface 125a onto mirror 127, is redirected by reflective surface 127a onto display 230.

Mirror 121 and surface 110a define a dihedral angle $\theta_a$. Mirror 127 and surface 110a define a dihedral angle $\theta_b$. In certain embodiments, angles $\theta_a$ and $\theta_b$ are about 135°. In a non-limiting embodiment, the dihedral angle between mirrors 123 and 125 is a right angle, i.e., the dihedral angle is about 90°.

Mirror 123 is substantially parallel to mirror 121, with a reflective side 123a having a facing relationship with the reflective side 121a of mirror 121. Mirror 125 is substantially parallel to mirror 127 with reflective side 125a having a facing relationship with reflective side 127a of mirror 127.

Further, in the illustrated embodiment of FIG. 2A, infrared (IR) emitter 270 is disposed adjacent eyepiece 126, and between mirrors 121 and 123. Similarly, the infrared emitter 260 is disposed adjacent eyepiece 128, and between the mirrors 125 and 127. As those skilled in the art will appreciate, infrared radiation IR is invisible to human eyes, and comprises wavelengths longer than those of visible light, extending from the nominal red edge of the visible spectrum at 700 nanometers (frequency 430 THz) to 1 mm (300 GHz). In a preferred embodiment, the IR emitters 260 and 270 operate at a wavelength of 940 nanometers, which eliminates any distraction to a testing subject.

Applicant has found that illuminating the eyes with infrared radiation eliminates unwanted artifacts in an eye image. The most distinctive feature in a recorded eye image is the contour of the pupil rather than limbus. Both the sclera and the iris strongly reflect infrared light, while only the sclera reflects visible light.

Applicant has further found that tracking the sharp contour of the pupil instead of the iris gives more reproducible results because the small size of the pupil makes it less likely to be occluded by an eyelid. Binocular viewer 110 and housing 120 are designed to block visible light. Therefore, infrared eye tracking can be employed without interference from visible light.

Referring to the illustrated embodiment of FIG. 2A again, housing 120 is attached to binocular viewer 110, and comprises video camera 240 which is in communication with controller 130 via communication link 242, video camera 250 which is in communication with controller 130 via communication link 252, and visual display 230 which is in communication with controller 130 via communication link 232. Video camera 240 transmits eye movement data in digital video frame to the controller 130 via communication link 242. In certain embodiments, digital video frame data is transferred by video camera 240 to controller 130 in a digital bit stream. In certain embodiments, digital video frame data is transferred by video camera 240 to controller 130 as a digitized analog signal.

Video camera 250 transmits eye movement data in digital video frame to the controller 130 via communication link 252. In certain embodiments, digital video frame data is transferred by video camera 250 to controller 130 in a digital bit stream. In certain embodiments, digital video frame data is transferred by video camera 250 to controller 130 as a digitized analog signal. In certain embodiments, the cameras 240 and 250 operate on fixed focus lenses, which are adjustable. In other embodiments, cameras 240 and 250 operate on auto focus lenses. In yet other embodiments, cameras 240 and 250 operate on telocentric lenses. In still other embodiments, cameras 240 and 250 operate on extended depth-of-field lenses.

In the illustrated embodiment of FIG. 2A, mirror 125 is disposed between video camera 240 and eyepiece 128. Mirror 125 and IR filter 150 are used to block the infrared radiation from bouncing back and interfering with the cameras. Infrared emitter 260 shines infrared light onto eye 202B, and video camera 240 is able to record the movement of eye 202B because of that infrared illumination.

In the illustrated embodiment of FIG. 2A, mirror 123 is disposed between video camera 250 and eyepiece 128. Mirror 123 and IR filter 152 are used to block the infrared radiation from bouncing back and interfering with the cameras. Infrared emitter 270 shines infrared light onto eye 202A, and video camera 250 is able to record the movement of eye 202A because of that infrared illumination.

Figure 6A:
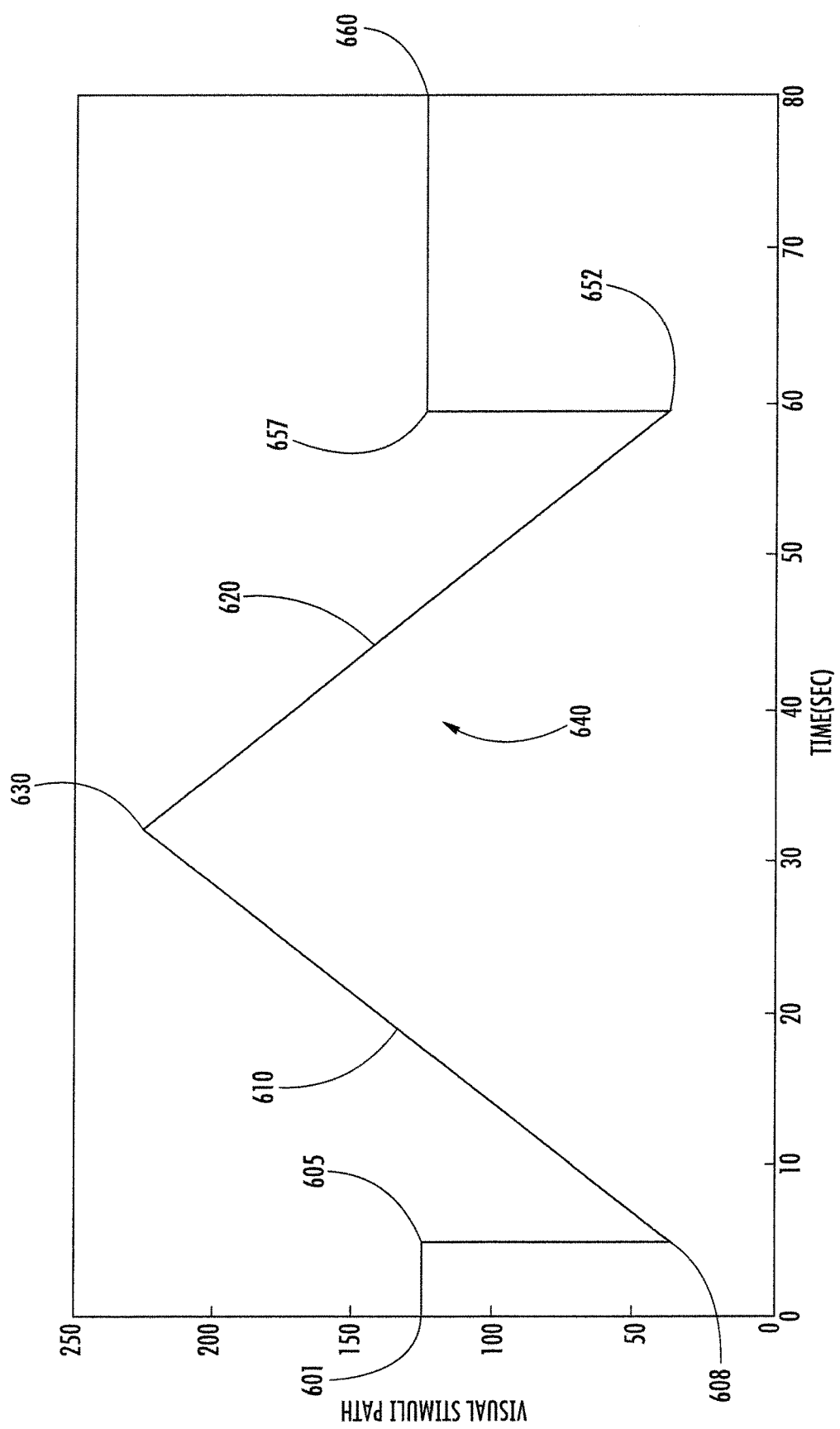
FIG. 6A is a graph illustrating a programmed visual stimulus path, according to the present disclosure.

Referring now to FIG. 6A, in certain embodiments controller 130 causes the displayed visual stimuli 234 and 236 to move convergently and divergently in an alternate manner using a preprogrammed visual stimulus path. In certain embodiments, visual stimuli 234 and 236 are initially substantially merged on the visual display device. Even though visual stimuli 234 and 236 are not actually merged on the display device, the subject perceives only a single image because the subject's brain has formed a single image from the two differing right eye image and left eye image. In other embodiments, visual stimuli 234 and 236 can start unconverged and move slowly into convergence.

The visual stimuli then move divergently, i.e. away from each other, in accord with curve 610 until a maximum separation is reached at point 630. At some point along curve 610, the subject's brain is unable to maintain a single image, and the subject perceives two different images.

Thereafter, visual stimuli 234 and 236 move convergently in accord with curve 620. At some point along curve 620, the subject's brain can once again form a single perceived image. In certain embodiments, the divergent movement of the visual stimuli, followed by convergent movement of those visual stimuli, takes about 90 seconds.

In certain embodiments, the beginning separation between visual stimuli 234 and 236 varies from about 120 to about 150 mm, and preferably at about 140 mm. In certain embodiments, the maximum separation between visual stimuli 234 and 236 at point 630 (FIG. 6A) varies from about 250 to about 310 mm, and preferably at about 300 mm.

In addition, the size of the stimuli 234 and 236 can be increased or decreased from one examination to another examination. Further, the brightness and the coloration of the stimuli 234 and 236 vary from one examination to another examination.

Referring to FIG. 6A, at point 601, i.e. at the beginning of the procedure, the visual stimuli are separated by about 125 mm for about 5 seconds. Immediately thereafter at point 605, the stimuli are instantly brought closer, i.e. to a separation of about 40 mm. At point 605, the stimuli begin to separate, i.e. diverge, at a speed of about 1 to 3 mm/second, with the preferred speed of about 2 mm/second as shown by linear curve portion 610 having a positive slope.

Figure 6B:
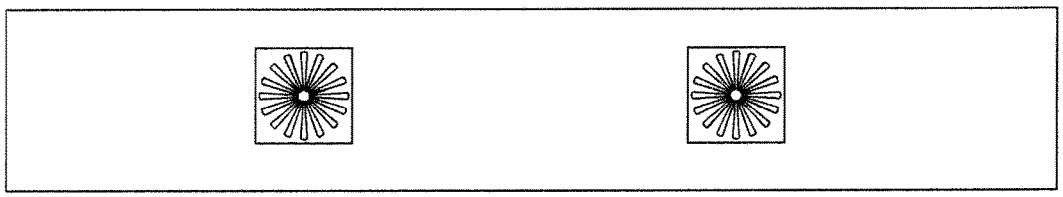
FIGS. 6B-6D are schematic diagrams showing the visual stimuli moving convergently and divergently, according to the present disclosure.
Figure 6C:
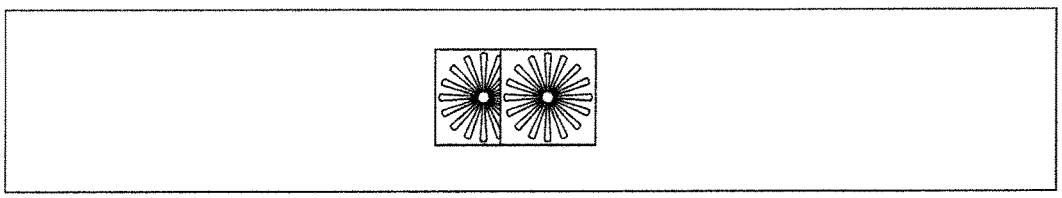
Figure 6D:
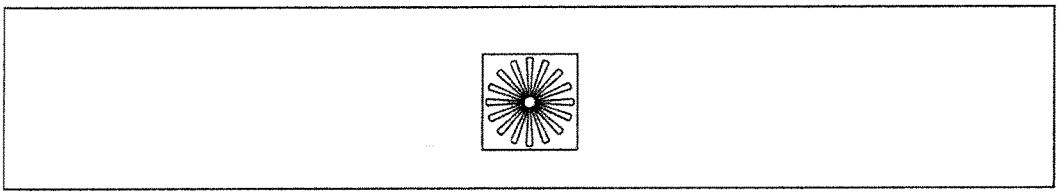

When visual stimuli 234 and 236 reach a maximum separation at point 630, which is about 230 mm on the visual display, the visual stimuli then converge, i.e. move towards each other (FIG. 6C). At point 657, the visual stimuli are separated by about 40 mm. Immediately thereafter, the stimuli move apart to a separation of about 125 mm for about 20 seconds, and the procedure ends.

In certain embodiments, the divergence/convergence process repeats two or more times to generate multiple sets of video frames of eye movement to determine the reproducibility of Applicant's apparatus and method.

In certain embodiments, visual display device 230 can be moved backwardly/forwardly. In certain embodiments, one or more iterations of Applicant's method summarized hereinabove are performed with visual display device 230 at a first distance from eyepieces 126 and 128. The visual display device is then repositioned at a second distance from eyepieces 126 and 128, and Applicant's procedure is repeated. In certain embodiments, the second distance is less than the first distance. In other embodiments, the second distance is greater than the first distance.

Referring now to FIG. 2B, in certain embodiments visual display device 230 can be move forwardly and/or backwardly within housing 120. Apparatus 205 comprises the elements of apparatus 200, and further comprises locomotion assembly 280a attached to a first end of visual display device 230. Locomotion assembly 280a is interconnected to controller 130 by communication link 284. Locomotion tracks 295a are positioned such that moveable wheels disposed on locomotion assembly 280a can be disposed on locomotion tracks 295a.

Apparatus 205 further comprises locomotion assembly 280b attached to a second end of visual display device 230. Locomotion assembly 280b is interconnected to controller 130 by communication link 282. Locomotion tracks 295b are positioned such that moveable wheels disposed on locomotion assembly 280b can be disposed on locomotion tracks 295b.

As described hereinabove, in certain embodiments Applicant's apparatus comprises two mirror and two visual display devices. For example, in the illustrated embodiment of FIG. 3A, apparatus 300 comprises two mirrors and two visual display devices.

Apparatus 300 comprises a first mirror 323 comprising reflective surface 323a. Mirror 323 is disposed between eyepiece 126 and video camera 250. Sight path 305a originates at eyepiece 126, and includes reflective surface 323a, and visual display device 324. Display device 320 is interconnected to controller 130 via communication link 322.

Apparatus 300 further comprises a second mirror 325 comprising reflective surface 325a. Mirror 325 is disposed between eyepiece 128 and video camera 240. Sight path 305b originates at eyepiece 128, and includes reflective surface 325a, and visual display device 314. Display device 310 is interconnected to controller 130 via communication link 312.

Figure 3A:
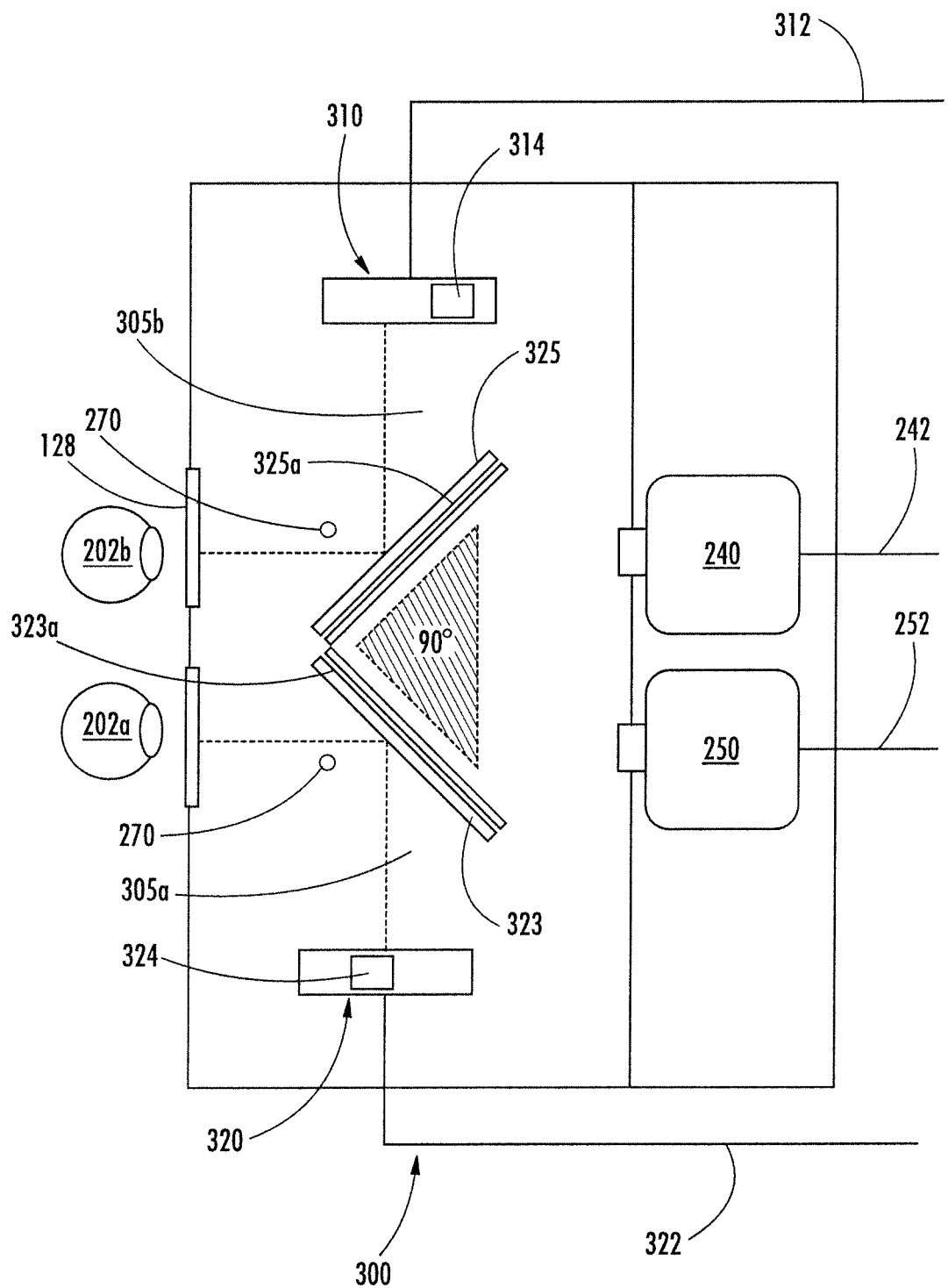
FIG. 3A is a schematic diagram of another embodiment of the binocular viewer and the housing comprising two visual displays, according to the present disclosure.
Figure 3B:
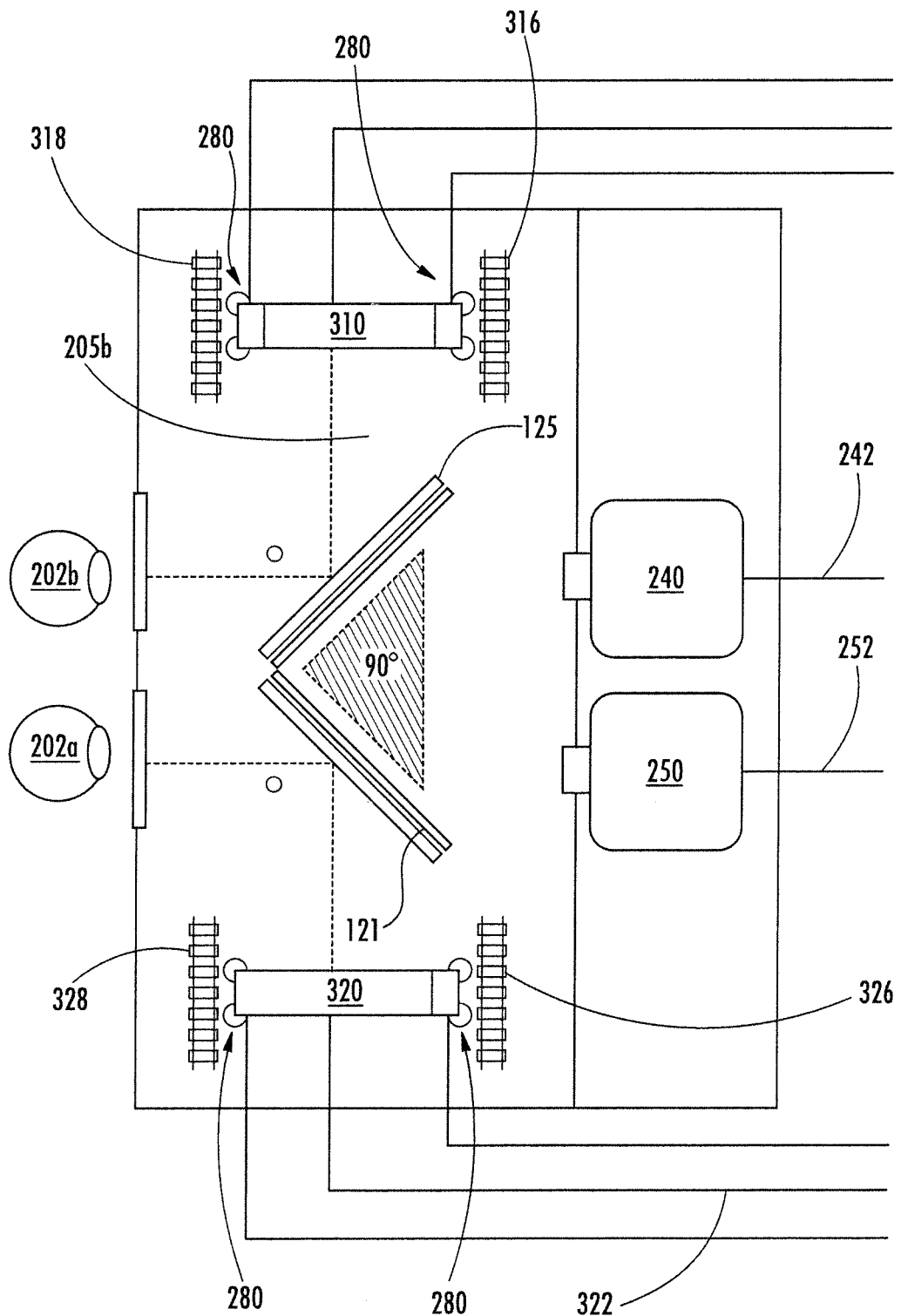
FIG. 3B is a schematic diagram of another embodiment of the binocular viewer and the housing comprising two movable visual displays, according to the present disclosure.

Referring now to FIG. 3B, apparatus 305 includes the elements of apparatus 300 (FIG. 3A) and further includes a first locomotion assembly 280c attached to a first end of visual display device 310. Locomotion assembly 280c is interconnected to controller 130 by communication link 315. Locomotion tracks 318 are positioned such that moveable wheels disposed on locomotion assembly 280c can be disposed on locomotion tracks 318.

Apparatus 305 further comprises locomotion assembly 280d attached to a second end of visual display device 310. Locomotion assembly 280d is interconnected to controller 130 by communication link 313. Locomotion tracks 316 are positioned such that moveable wheels disposed on locomotion assembly 280d can be disposed on locomotion tracks 316.

Similarly, apparatus 305 comprises a third locomotion assembly 280e attached to a first end of visual display device 320, which is interconnected to controller 130 via communication link 322. Locomotion assembly 280e is interconnected to controller 130 by communication link 328. Locomotion tracks 319 are positioned such that moveable wheels disposed on locomotion assembly 280e can be disposed on locomotion tracks 319. In addition, a fourth locomotion assembly 280f attached to a second end of visual display device 320. Locomotion assembly 280f is interconnected to controller 130 by communication link. Locomotion tracks 317 are positioned such that moveable wheels disposed on locomotion assembly 280f can be disposed on locomotion tracks 317.

Figure 4:
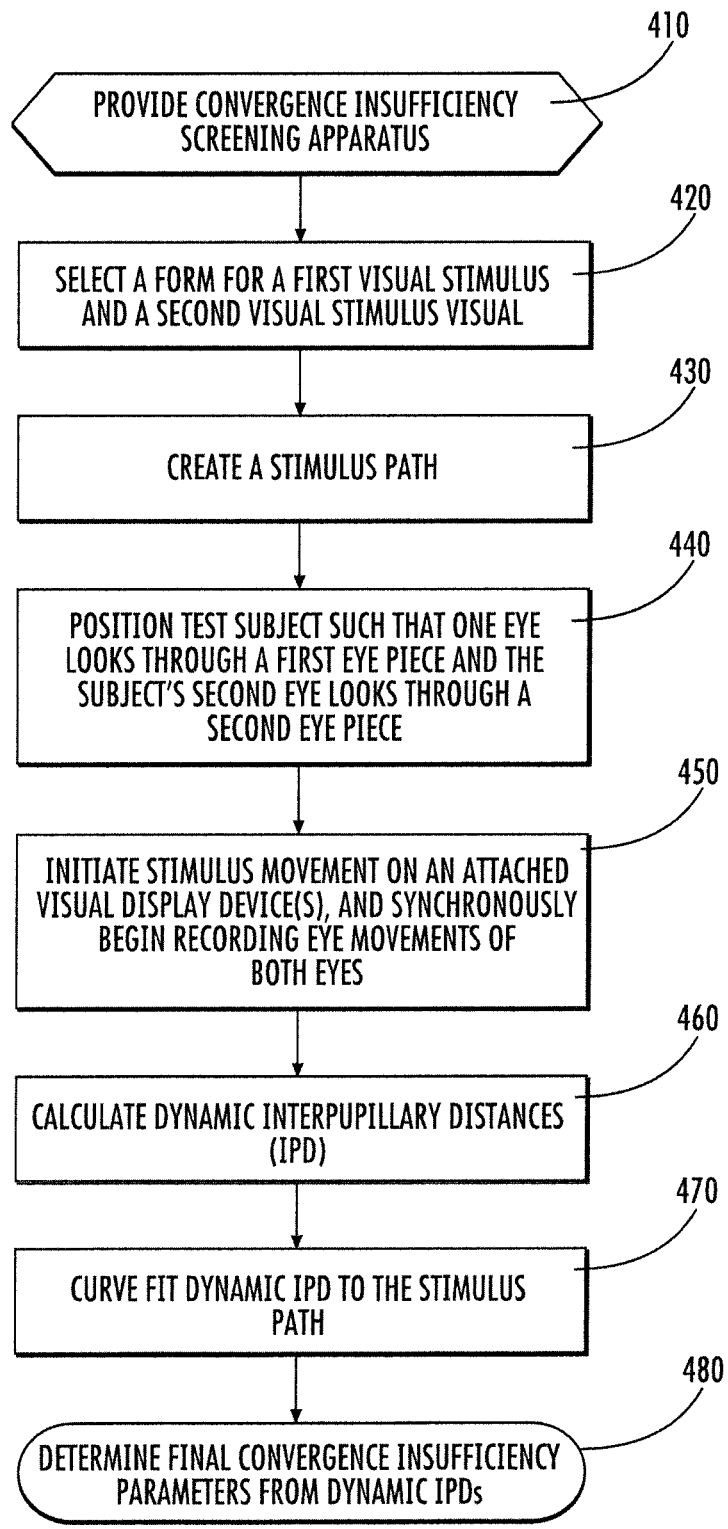
FIG. 4 is a flowchart showing a method to objectively screen for CI, according to the present disclosure.

FIG. 4 summarizes the steps of Applicant's method using Applicant's apparatus. In step 410, the method provides an apparatus configured to screen subjects for convergence insufficiency. In certain embodiments, the method in step 410 provides apparatus 200 (FIG. 2A). In certain embodiments, the method in step 410 provides apparatus 205 (FIG. 2B). In certain embodiments, the method in step 410 provides apparatus 300 (FIG. 3A). In certain embodiments, the method in step 410 provides apparatus 305 (FIG. 3B).

In step 420, the method selects a form for a first visual stimulus. Further in step 420, the method selects a form for a second visual stimulus. In certain embodiments, the form selected for the first visual stimulus is identical to the form selected for the second visual stimulus. For example, FIG. 6B shows a first visual stimulus and a second visual stimulus, wherein the first visual stimulus comprises the same form as the second visual stimulus. In other embodiments, the form selected for a first visual stimulus differs from the form selected for a second visual stimulus.

In step 430, the method creates a stimulus path. For example, an illustrated stimulus path is depicted in FIG. 6A. Further, the size, the brightness, the beginning distance, and the moving speed of the two stimuli are determined in step 430.

In step 440, a testing subject 102 positions his or her eyes to look into eyepieces 126 and 128 disposed in binocular viewer 110. In step 450, the method initiates visual stimulus movement on one or more attached visual display devices. In addition, the method synchronously begins recording eye movement of both eyes.

In certain embodiments, a controller attached comprising a portion of the screening apparatus of step 410 performs step 430. In certain embodiments, a controller attached to the screening apparatus wirelessly receives an instruction to perform step 430.

In certain embodiments, recorded video frames of the eye movements of eye 202A and eye 202B are stored in a non-transitory computer readable medium 1520 (FIG. 15) by a processor 1510 (FIG. 15) disposed in controller 130. In certain embodiments, computer readable medium 1520 comprises a magnetic storage medium, an optical storage medium, or an electronic storage medium. By electronic storage medium, Applicant means a PROM, EPROM, EEPROM, Flash PROM, compactflash, smartmedia, and the like.

In certain embodiments, the data calculation in steps 460, 470, and 480 can be performed after the examination. In other embodiments, the data calculation in steps 460, 470, and 480 can be performed in real time during the examination. In yet other embodiments, the data calculation in steps 460, 470, and 480 can be performed in slightly delayed real time during the examination. In step 460, the method determines an interpupillary distance (IPD). IPD is the distance between the centers of the pupils of the two eyes. In certain embodiments, step 460 is performed by controller 1500 using processor 1510, and microcode 1522, and instructions 1524. In certain embodiments, controller 1500 wirelessly receives an instruction to perform step 460.

In step 470, the method graphically curve fits a plot of IPD versus time. Now referring to FIG. 11, the method converts the IPDs in pixel numbers (FIG. 10) to x coordinates in millimeters (mm). A curve 1110 is a display of IPDs in mm versus time in seconds. Further, a substantially linear portion 1120 of the curve 1110 comprising a positive slope and another substantially linear portion 1130 of the curve 1110 comprising a negative slope are identified. Additionally, random sample consensus (RANSAC), an iterative method to estimate parameters of a mathematical model from a set of observed data which contains errors and/or outliers, is used to remove errors and/or outliers and optimize the curve 1110.

Figure 12:
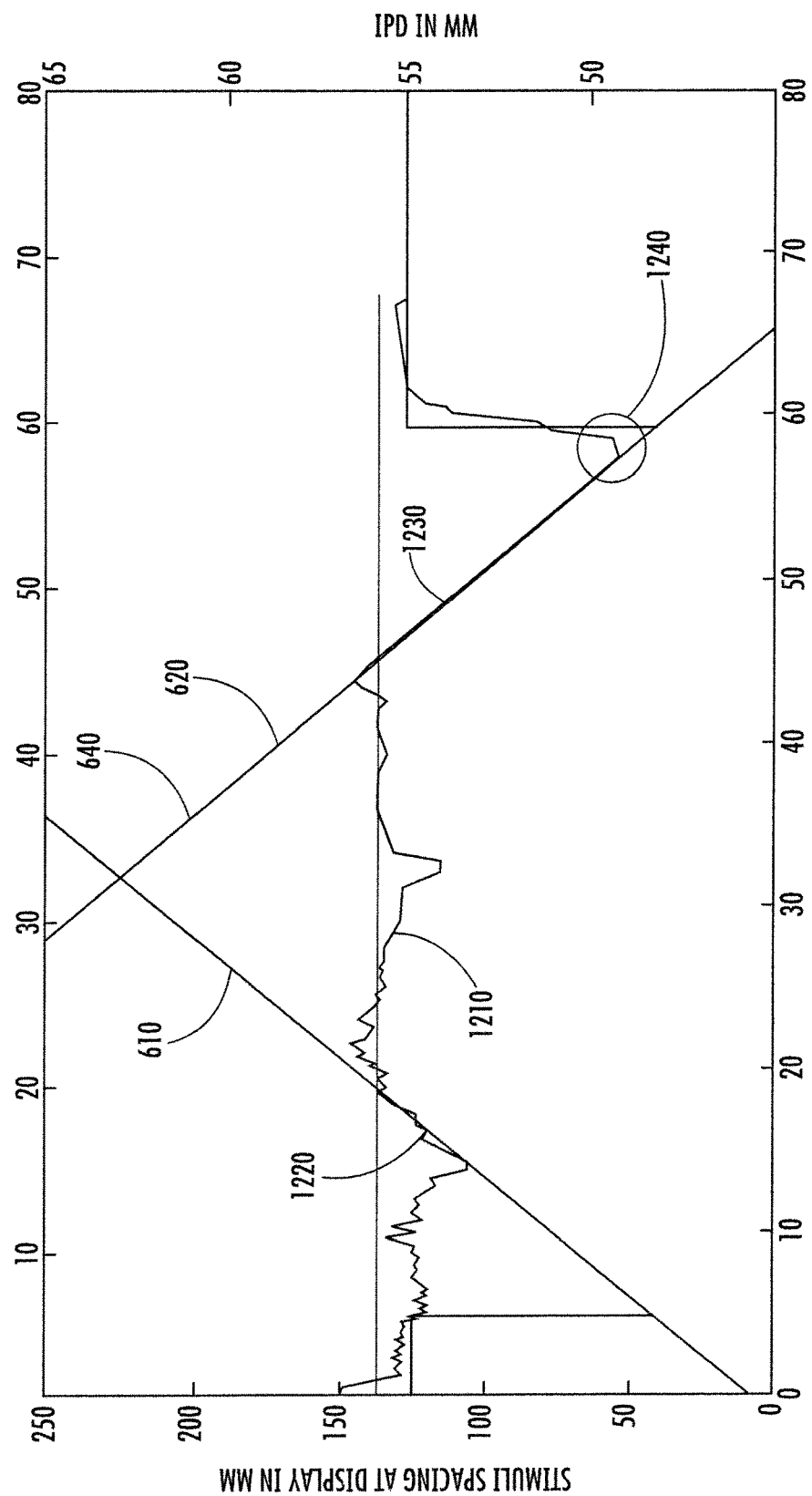
FIG. 12 is a graph of dynamic IPDs in millimeters versus times with an adjusted y-axis scale, according to the present disclosure.
Figure 16A:
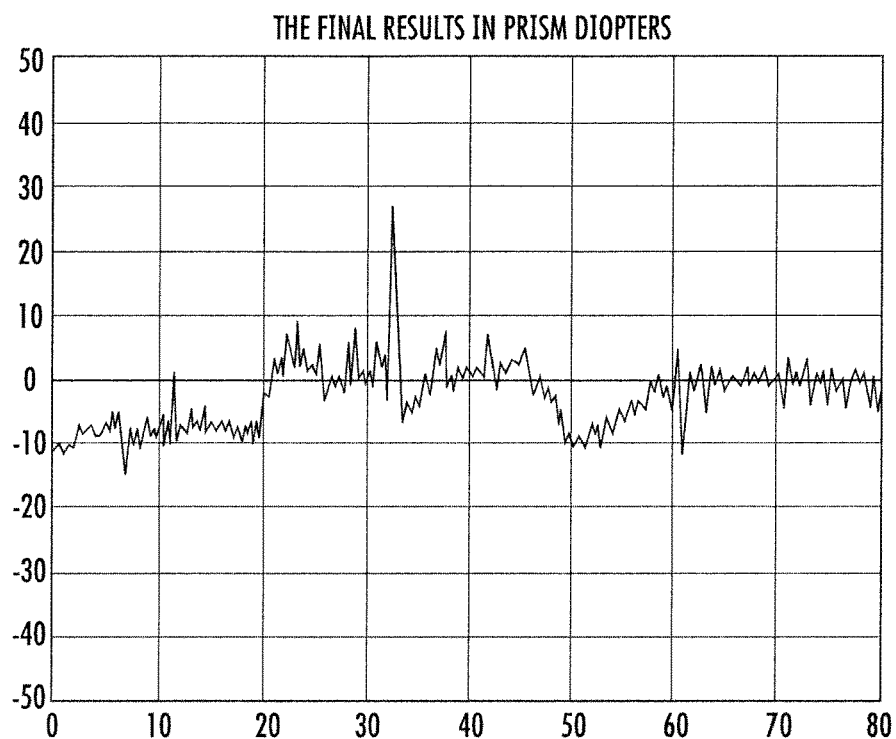
FIGS. 16A and 16B are graphs of testing results in prism diopters, according to the present disclosure.
Figure 16B:
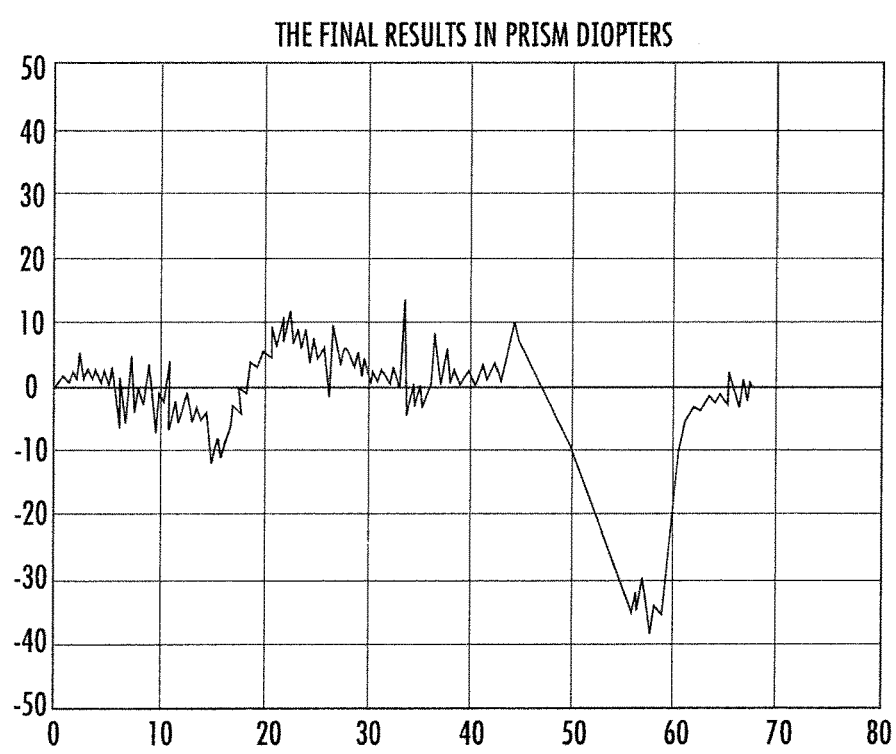

Further in step 470 and referring to FIG. 12, an optimal curve 1210 of dynamic IPDs is generated by further adjusting the scale of the y-axis in mm. The optimal curve 1210 is overlapped with the visual stimulus path 640. Further, a substantially linear portion 1220 comprising a positive slope of the curve 1210 overlays with the positive slope 610 of the visual stimulus path 640 and another substantially linear portion 1230 comprising a negative slope of the curve 1210 overlays with the negative slope 620 of the visual stimulus path 640. Moreover, point 1240, which is the lowest value of a dynamic IPD on curve 1210, is the point at which the stimuli appear to have merged for the testing subject and the point at which the testing subject's convergence should be at its maximum capacity. For example, when the substantially linear portion 1230 is long and the valley 1240 reaches down lower towards the x-axis, the testing subject is able to maintain convergence of the stimuli for a long time during the moving stimuli test, therefore, the testing subject is not convergence insufficient. Referring to FIG. 16B, a testing subject has a dynamic IPD of about −35 prism diopters and displays a good convergence. A range of −20 to −40 prism diopters in dynamic IPD is considered a range displaying good convergence. However, when the substantially linear portion 1230 is short and the valley 1240 does not reach down far towards the x-axis, the testing subject is not able to maintain convergence of the stimuli for a long time during the test, therefore, the testing subject may have CI. Referring to FIG. 16A, a different testing subject has a dynamic IPD of −15 prism diopters and displays a poor convergence.

Figure 13C:
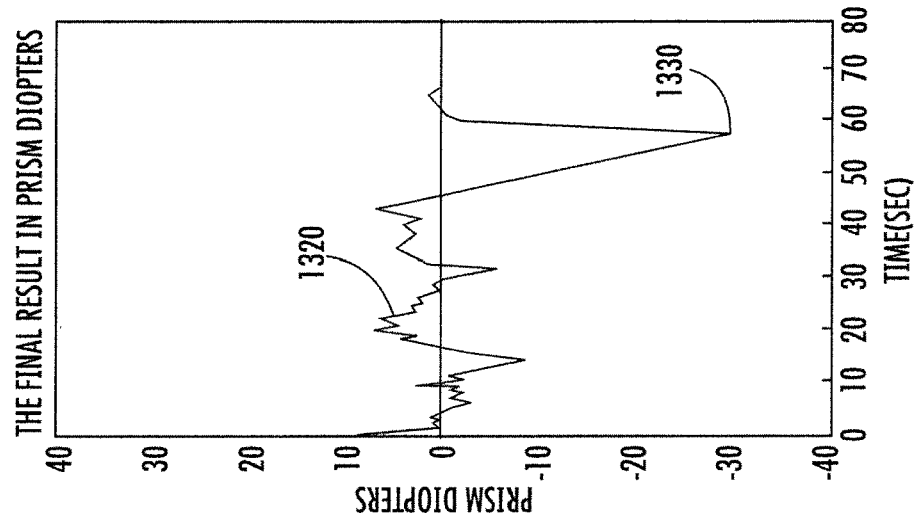
FIGS. 13A-13C are graphs showing dynamic IPDs in degrees and prism diopters versus time, according to the present disclosure.
Figure 13B:
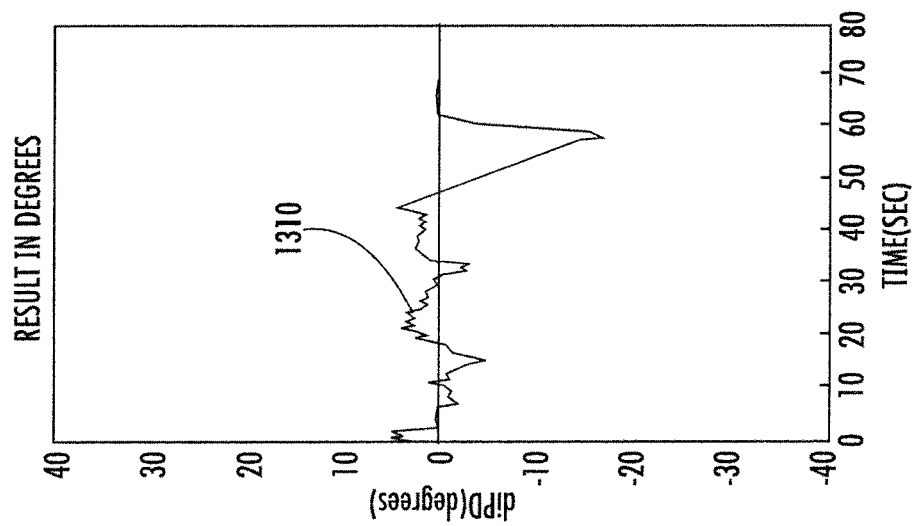
Figure 13A:
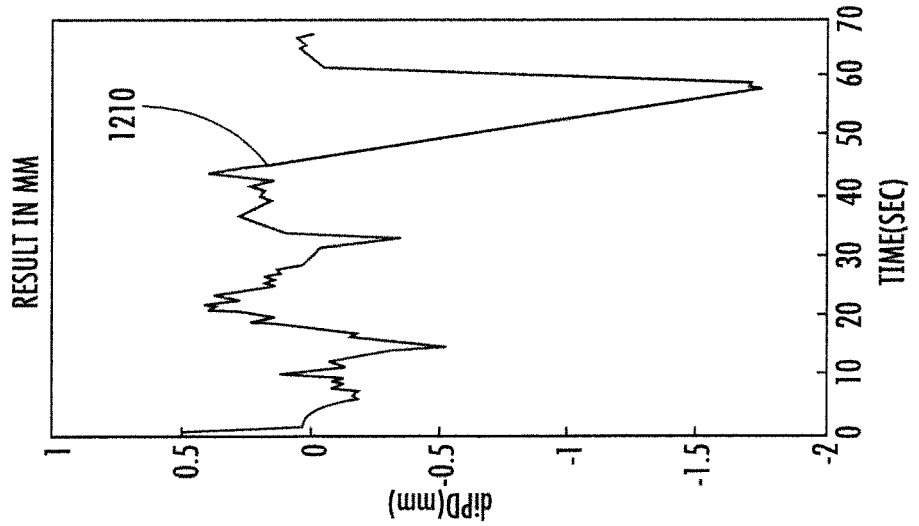

Referring to FIGS. 13A-13C, the curve 1210 with dynamic IPDs in mm is transitioned to a curve 1310 with dynamic IPDs in degrees. Further, the curve 1310 with dynamic IPDs in degrees is transitioned to a curve 1320 with dynamic IPDs in prism diopters. An antapex 1330 indicates the testing subject's maximum amount of convergence in prism diopters to the stimuli and is used as the primary determinant for CI.

In certain embodiments, step 470 is performed by controller 1500 using processor 1510, and microcode 1522, and instructions 1524. In certain embodiments, controller 1500 wirelessly receives an instruction to perform step 470.

In step 480, the method determines a dynamic IPD for the test subject. In certain embodiments, step 480 is performed by controller 1500 using processor 1510, and microcode 1522, and instructions 1524. In certain embodiments, controller 1500 wirelessly receives an instruction to perform step 480.

Figure 5:
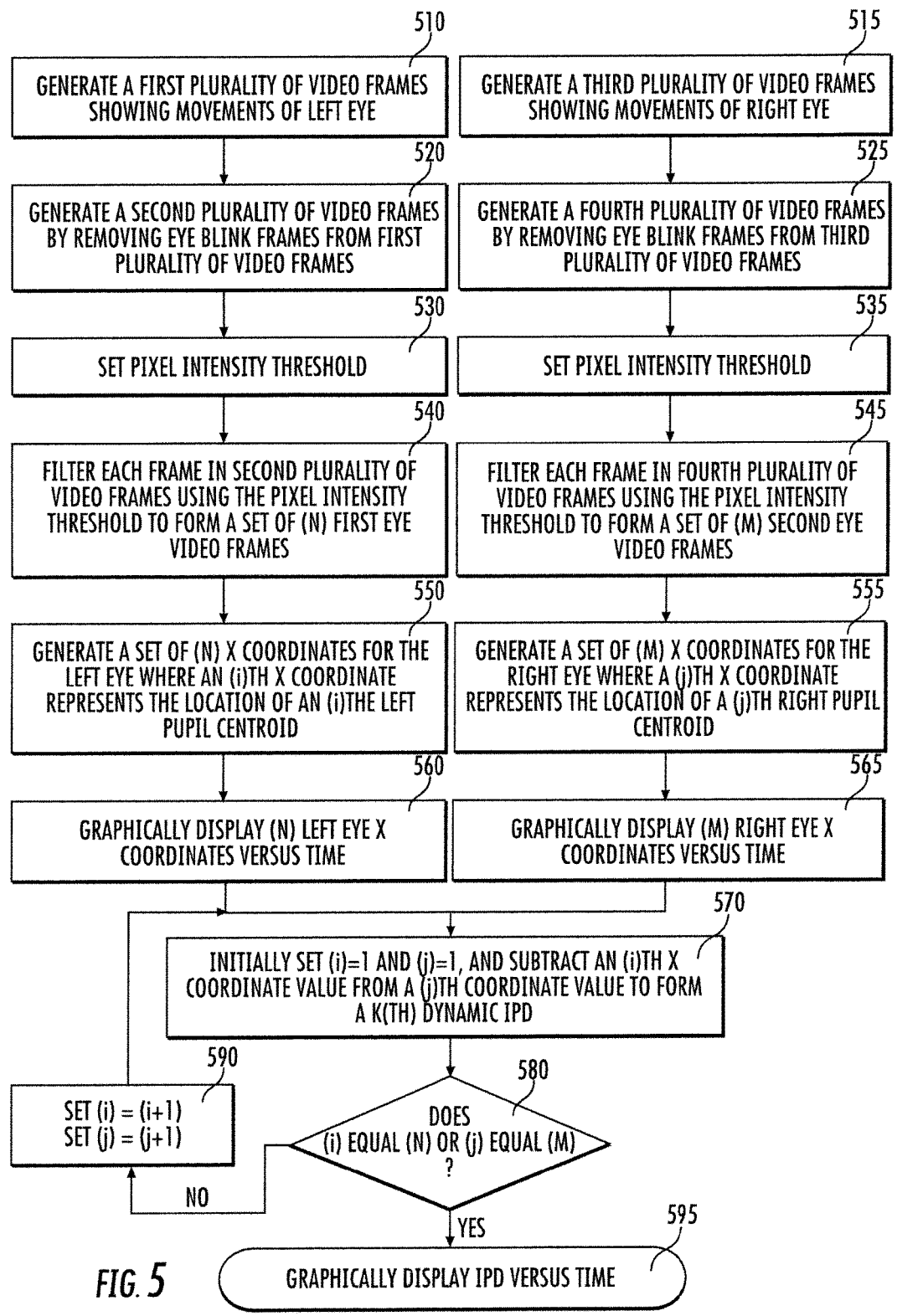
FIG. 5 is a flowchart showing a method to process and analyze eye movement data recorded by cameras, according to the present disclosure.

In certain embodiments, step 460 comprises the steps recited in FIG. 5.

Figure 7:
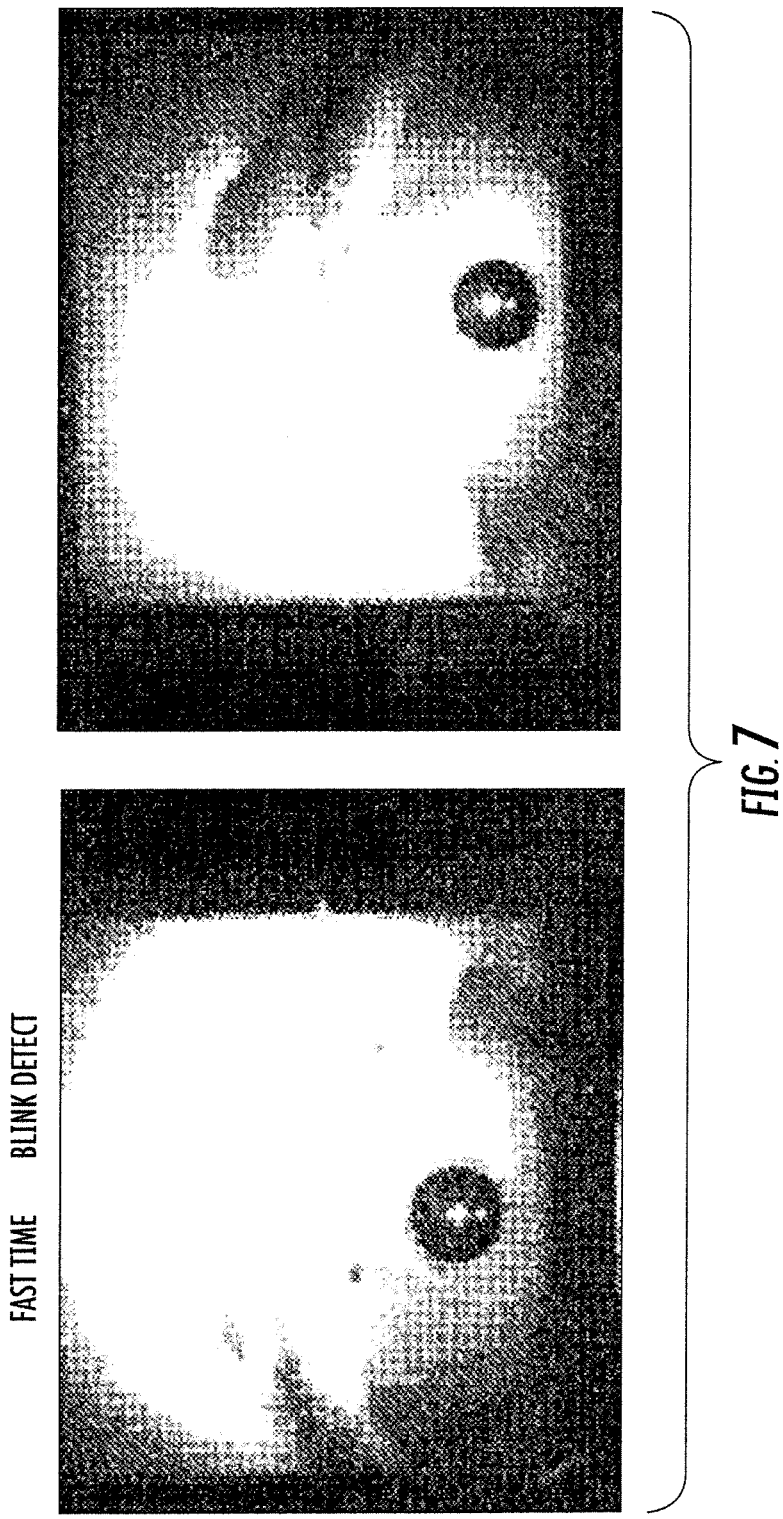
FIG. 7 are analog video frames of recorded eye movement at a certain time point, according to the present disclosure.
Figure 8:
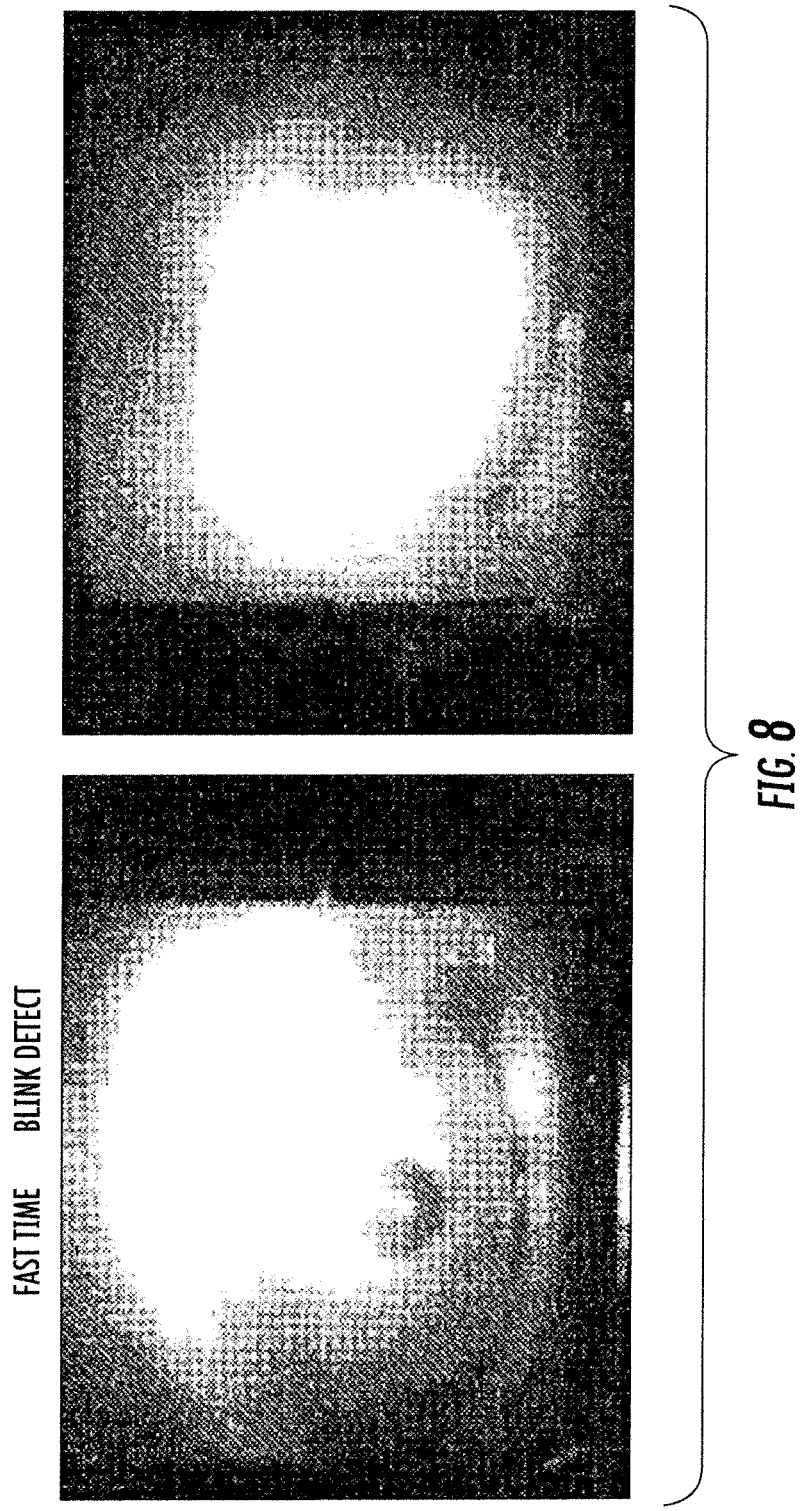
FIG. 8 are analog video frames of recorded eye movement during a blink, according to the present disclosure.

Referring to the illustrated embodiment in FIG. 5, step 510, video camera 250 records the movements of eye 202B and generates a plurality of video frames during the visual stimuli path described in step 430 (FIG. 4) Video camera 240 records the movements of eye 202A and generates a plurality of video frames during the visual stimuli path described in step 430 (FIG. 4). In certain embodiments, the frequency of the recorded video frames is about 0.1 sec per frame. A video frame at a certain time point is illustrated in FIG. 7. Referring now to FIG. 8, an eye blink is detected, and the video frame of the blink is further removed from the plurality of video frames generated in step 510 and step 515. Some testing subjects blink more frequently and use blinking as a way to reset the convergence system in their eyes. Applicant's apparatus is able to record the frequency and specific times of occurred blinks, which are additional information that can be utilized to determine CI.

Referring to FIGS. 9A-9D, the illustrated embodiment of the eye images demonstrates a test analysis sequence. In step 530 and 535, analog picture frames (FIG. 9A) are directly provided by camera 240 and 250, respectively. In steps 530 and 535, the method sets a pixel intensity threshold. A pixel intensity threshold is set by a computer readable program. In certain embodiments, the computer readable program is MATLAB. In certain embodiments, steps 530 and 535 are performed by controller 1500 using processor 1510, and microcode 1522, and instructions 1524. In certain embodiments, controller 1500 wirelessly receives an instruction to perform steps 530 and 535.

Figure 9A:
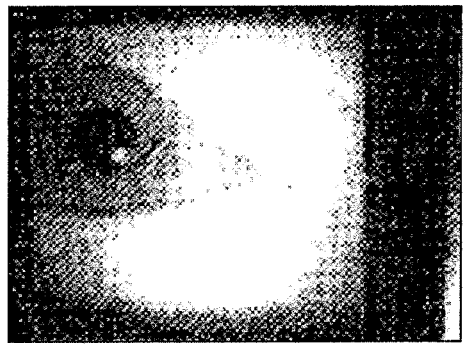
FIGS. 9A-9D are eye movement images, according to the present disclosure.
Figure 9B:
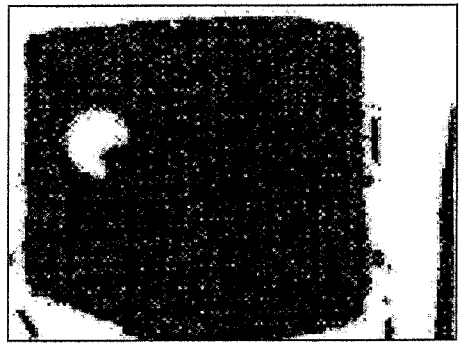
Figure 9C:
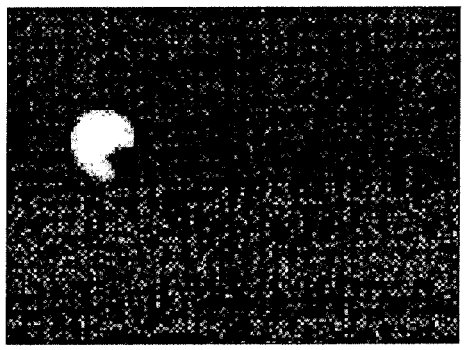
Figure 9D:
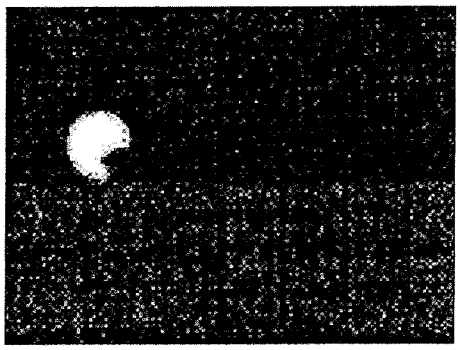

In steps 540 and 545, the method applies the pixel intensity threshold of steps 530 and 535, respectively, to each analog video frame to form a binary eye image illustrated in FIG. 9B comprising a black background and a white 202A or 202B eye image. Further, as illustrated in FIG. 9C, the borders of the binary eye image and small blobs (small white spots embedded in the black background) are cleared to form a uniform black background, as illustrated in FIG. 9D. Further, referring to FIG. 9D, the x-axis and the y-axis coordinates in pixel numbers of the white eye blob are determined by the computer readable program. This illustrated test analysis is repeated with every analog video frame until the last frame of either eye 202A or 202B to generate a plurality of N video frames of eye 202A and a plurality of M video frames of eye 202B.

In steps 550 and 555, the method generates a plurality of x coordinate values of eye 202A and 202B respectively are determined. An (i)th x coordinate data represents the location of an (i)th pupil centroid of the eye 202A and a (j)th x coordinate data represents the location of an (j)th pupil centroid of the eye 202B. In certain embodiments, steps 550 and 555 are performed by controller 1500 using processor 1510, and microcode 1522, and instructions 1524. In certain embodiments, controller 1500 wirelessly receives an instruction to perform step 550 and 555.

Figure 10:
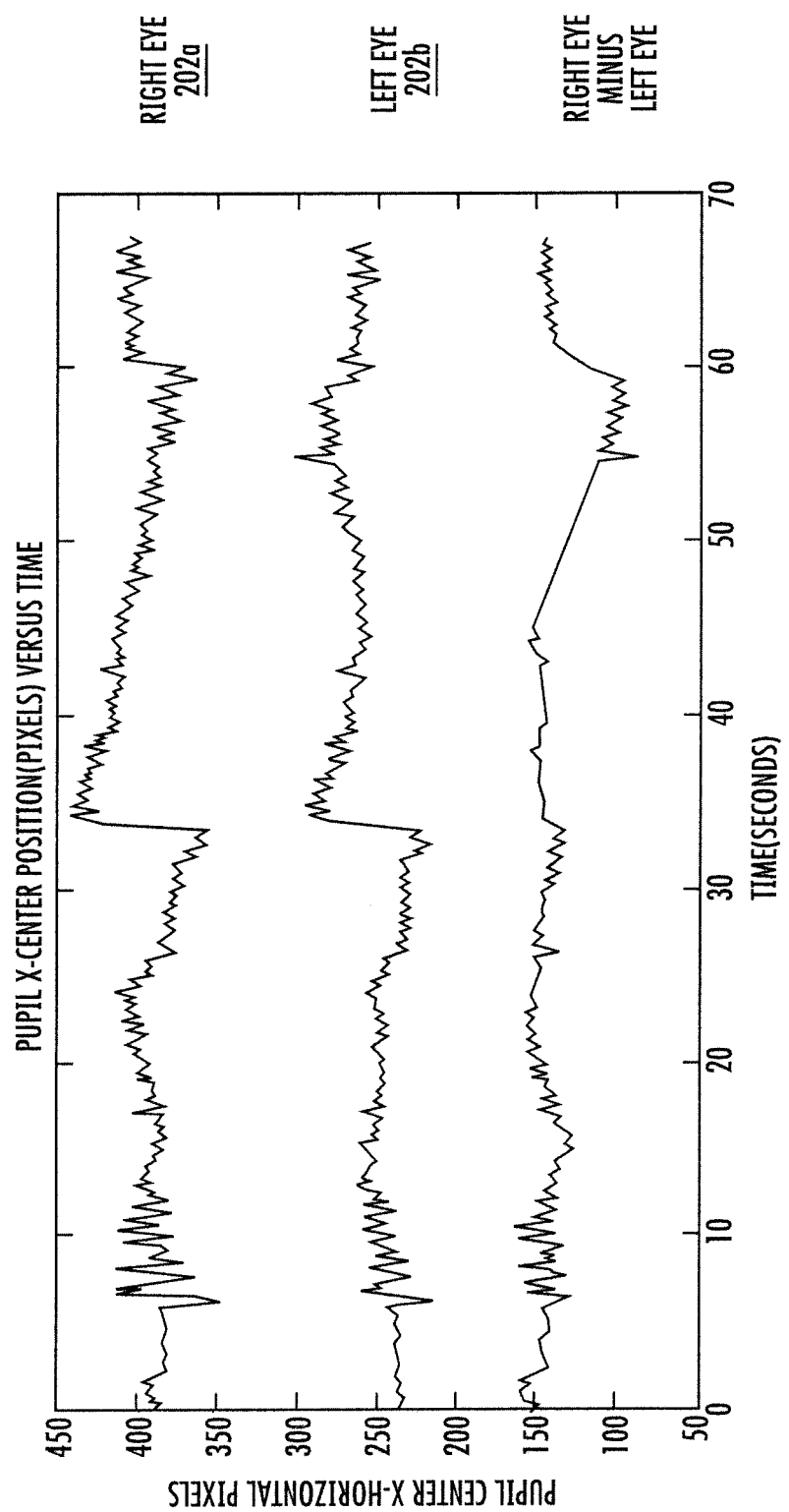
FIG. 10 is a graph of pupil positions in pixel numbers versus time and IPDs in pixel numbers versus time, according to the present disclosure.
Figure 11:
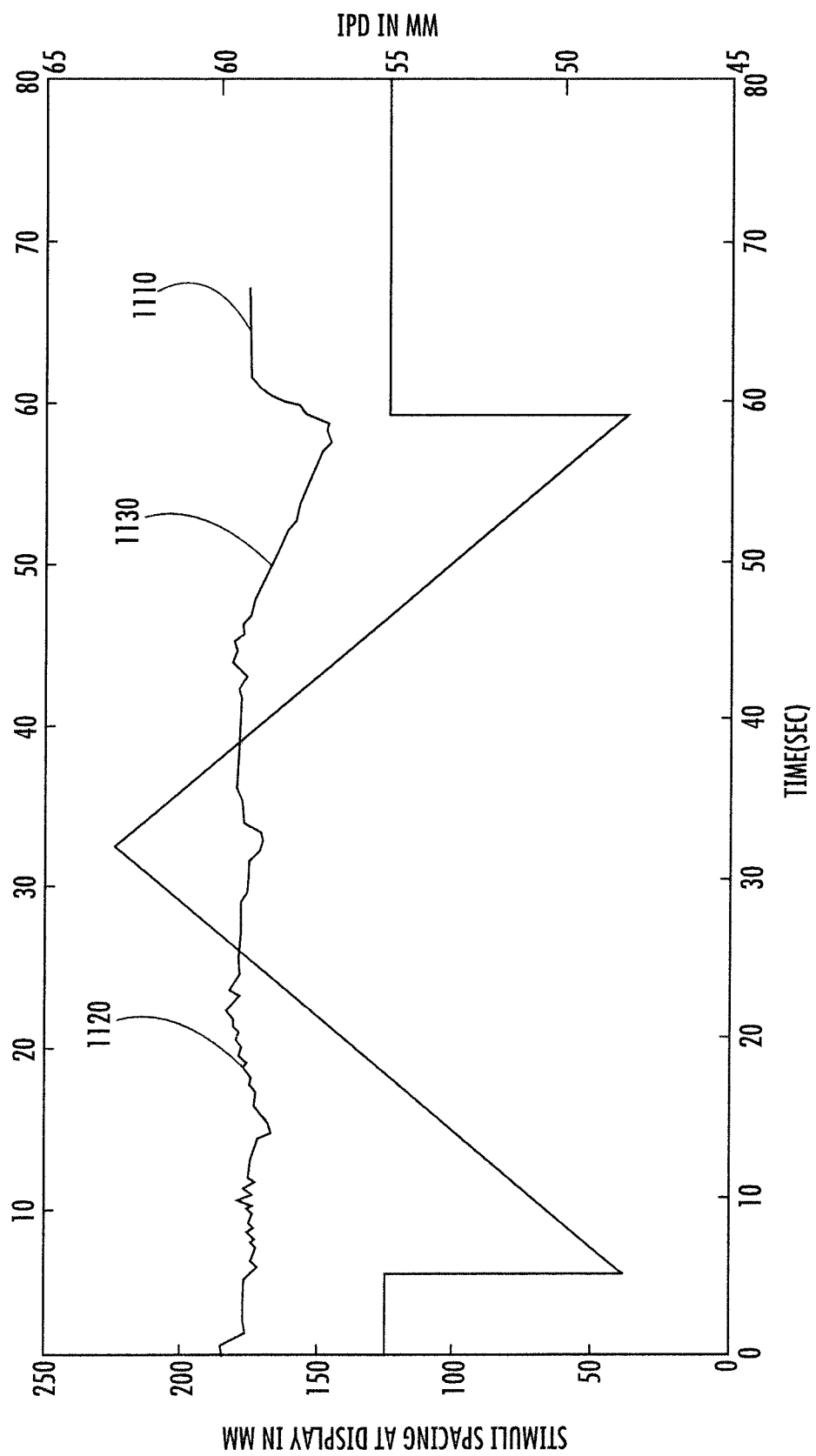
FIG. 11 is a graph of IPDs in millimeters versus time, according to the present disclosure.

Referring to FIG. 10, in steps of 570 and 575 the method graphically displays a first graph comprising left eye x coordinates versus time. The method further graphically displays a second graph comprising right eye x coordinates versus time. In certain embodiments, steps 570 and 575 are performed by controller 1500 using processor 1510, and microcode 1522, and instructions 1524. In certain embodiments, controller 1500 wirelessly receives an instruction to perform steps 570 and 575.

In step 570, the method for each time value, subtracts a left eye x coordinate from a right eye x coordinate to form a IPD for that time value. In certain embodiments, step 570 is performed by controller 1500 using processor 1510, and microcode 1522, and instructions 1524. In certain embodiments, controller 1500 wirelessly receives an instruction to perform step 570.

FIG. 10 illustrates a first graph showing right eye determined centroids versus time. FIG. 10 illustrates a second graph showing left eye determined centroids versus time. FIG. 10 further illustrates a third graph which comprises for each time value, the difference between a left eye x coordinate for that time value from a right eye x coordinate for that time value.

Figure 14:
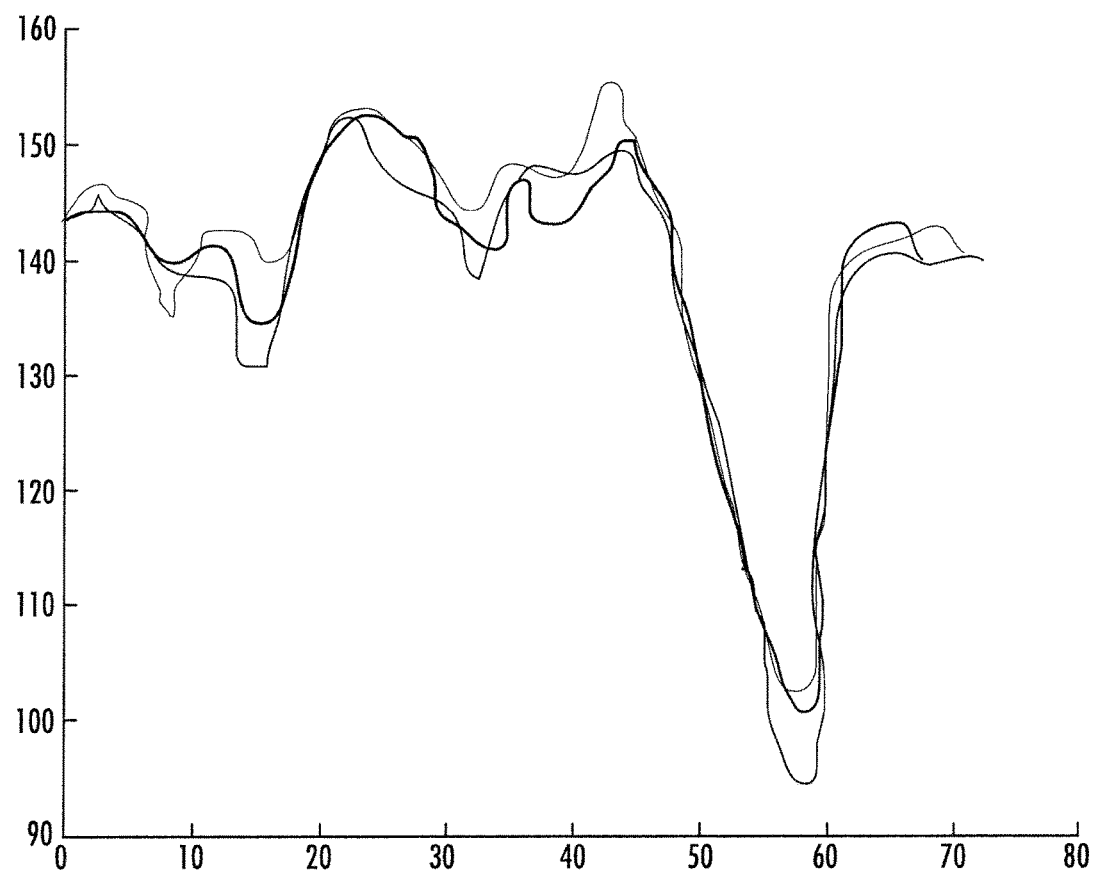
FIG. 14 is a graph of pupil positions in millimeters versus time of different sets of recorded eye movement during different cycles of visual stimuli convergence and divergence displaying, according to the present disclosure.

In step 590 and referring to FIG. 10, the dynamic IPDs calculated in step 570 are graphically displayed versus time. In the illustrated embodiment of FIG. 14, three curves of dynamic IPDs versus time from different sets of video frames of eye movement recorded during different process of visual stimuli' divergence and convergence match each other substantially, which demonstrates a strong reproducibility of the Applicant's method in screening for Convergence Insufficiency.

While the preferred embodiments of the present invention have been illustrated in detail, it should be apparent that modifications and adaptations to those embodiments may occur to one skilled in the art without departing from the scope of the present invention.

Figure 17:
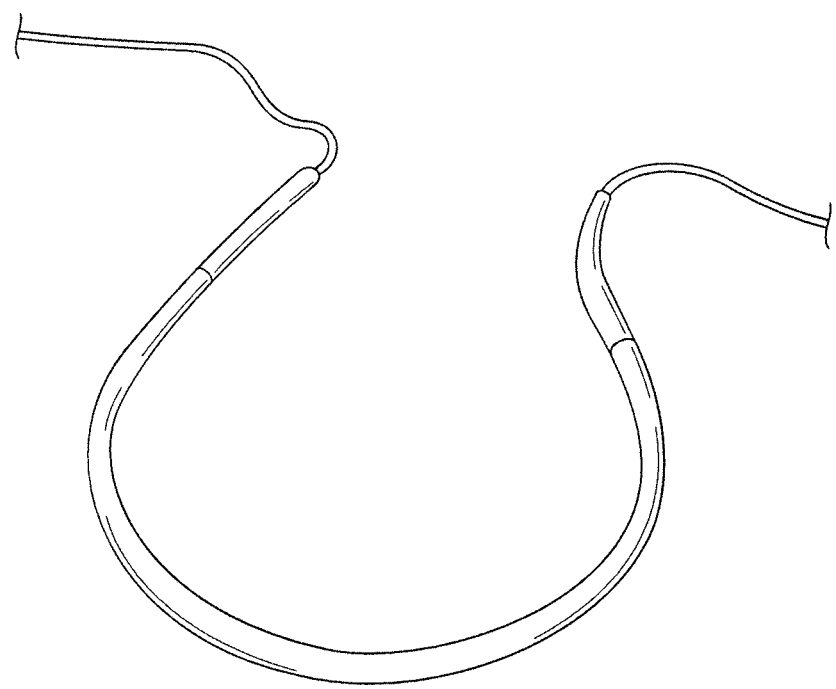
FIGS. 17-18 are images of example embodiments of the binocular viewer and associated equipment.
Figure 18:
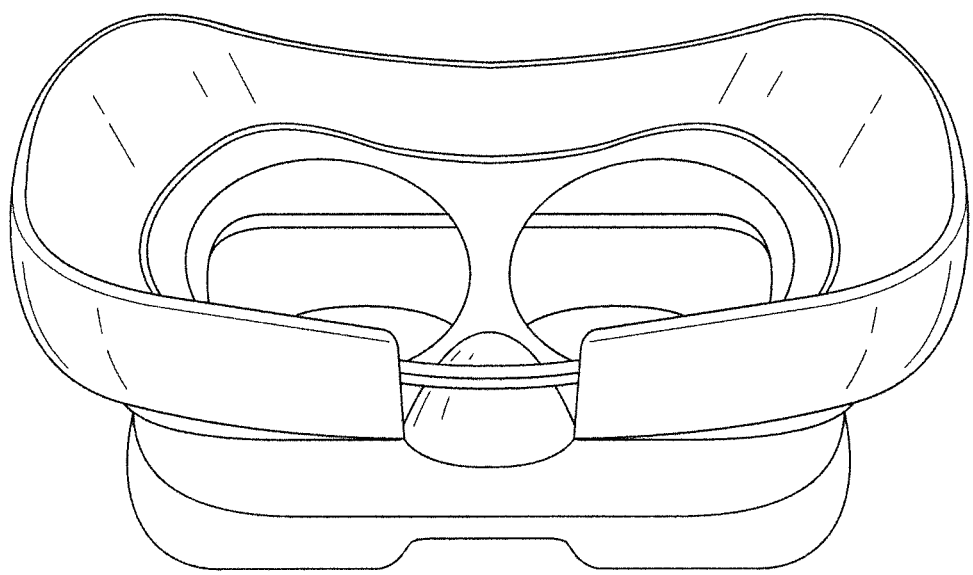

Referring now to FIGS. 17-18, a desirable product requirement of a CI screener is the ability to make measurements on a subject with prescription eyeglasses or contact lenses. As shown in FIG. 2A, using one IR light emitting diode (LED) per eye, this method works well without glasses or with contact lenses, providing a distinctive glint reflection that is easy to detect using established machine vision methods. However, this does not work well while wearing prescription glasses because the prescription lenses also reflect the infrared light, creating an additional glint blocking and obscuring the camera view of the glint/pupil/eye.

A standard way to suppress the glasses' reflection is to use a diffuse lighting illumination configuration. This is typically done with a ring structure of LEDs. However, this may be expensive, requiring multiple LEDs in a complex mechanical ring mount. Even more importantly, it may raise eye safety concerns with so many LEDs in close proximity to the eye.

FIG. 17 shows a unique diffuse illumination method composed of a flexible side glow optical fiber that has a superb light transmission for bright and consistent illumination using one or two LEDs. When mounted in an eye mask in a ring or oval configuration as shown in FIG. 18, it creates a diffuse eye illumination method that suppresses glint reflections from the eyeglasses as well as the eye. Of course, these features could be added to any of the above embodiments.

Explicit Near Point Convergence Test Disclosure

Figure 19:
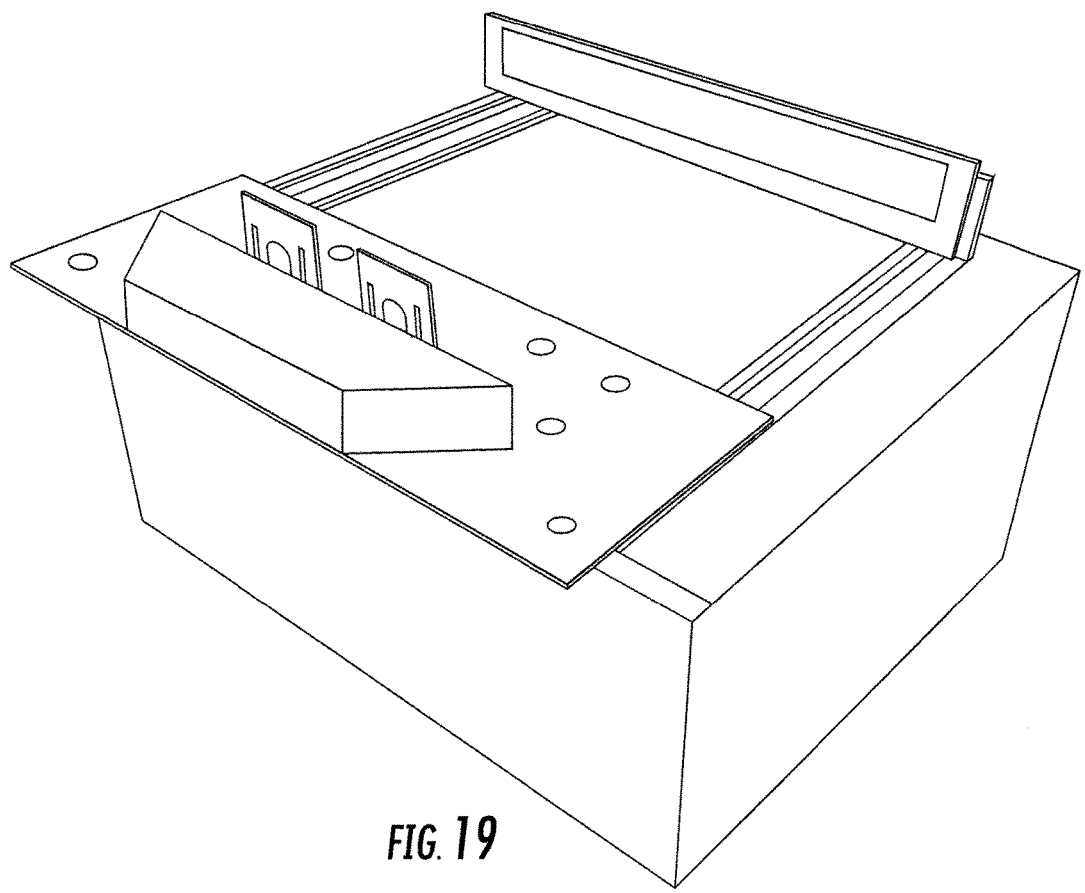
FIG. 19 is an image of an example embodiment for testing the device, according to the present disclosure.

Referring now to FIG. 19, the standard clinical methods to screen for CI include a near point convergence test. This test requires a subject to adjust his focus as well as his convergence while a visual stimulus is moved in toward his nose. In this way, the subject's ability to simultaneously accommodate and converge is dynamically tested.

FIG. 2B shows a mechanical configuration which allows the system to explicitly mimic the clinical near point test. Technically, it is a single visual stimulus display configuration with a variable image distance, all under computer control. FIG. 19 shows an example embodiment prototype.

Other features relating to screening devices are disclosed in co-pending application: titled "DEVICE FOR SCREENING CONVERGENCE INSUFFICIENCY AND RELATED METHODS," U.S. Pat. No 15/697,838, which is incorporated herein by reference in its entirety.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

That which is claimed is:

1. A device for screening a person for convergence insufficiency (CI) with a viewer, the device comprising:
a display adjacent the viewer; and
a processor and associated memory cooperating with said display and configured to
record movement of a first eye,
record movement of a second eye,
display on said display a first visual stimulus and a second visual stimulus,
cause, in alternating fashion, convergent movement and divergent movement in the first visual stimulus and the second visual stimulus along a visual stimulus path,
record dynamic movement of the first eye along the visual stimulus path,
record dynamic movement of the second eye along the visual stimulus path,
determine respective centroid positions of the second eye and the first eye during the convergent and divergent movement of the first visual stimulus and the second visual stimulus based on the recorded dynamic movements of the first eye and the second eye,
calculate from the respective centroid positions a plurality of interpupillary distances (IPDs) over time, and from the plurality of the IPDs, generate dynamic IPDs over time, and
compare the dynamic IPDs with the visual stimulus path to serve as an indicator for whether the person has CI.

2. The device of claim 1 wherein a duration of each of the convergent movement and the divergent movement is 80-100 seconds.

3. The device of claim 1 further comprising a first infrared (IR) source configured to irradiate the first eye and a second IR source configured to irradiate second eye; and wherein said processor and memory are configured to generate a first plurality of video frames showing movement of the first eye, and generate a second plurality of video frames showing movement of the second eye.

4. The device of claim 3 wherein said processor and memory are configured to:
identify second blink pixels comprising second eye blinks in the second plurality of video frames;
form a third plurality of video frames by removing the second blink pixels from the second plurality of video frames;
identify first blink pixels comprising first eye blinks in the first plurality of video frames; and
form a fourth plurality of video frames by removing the first blink pixels from the first plurality of video frames.

5. The device of claim 3 wherein said processor and memory are configured to generate the first plurality of video frames by performing at least:
filtering each of the first plurality of video frames using a pixel intensity threshold to form a third plurality of video frames, each of the third plurality of video frames comprising a black background in combination with a white background, a first eye image, the third plurality of video frames comprising an N number of video frames;
filtering each of the second plurality of video frames using the pixel intensity threshold to form a fourth plurality of video frames, each of the fourth plurality of video frames comprising a black background in combination with a white background, a second eye image, the fourth plurality of video frames comprising an M number of video frames;
determining, for each of the third plurality of video frames, x and y coordinates for a first eye pupil centroid; and
generating a first plurality of x coordinate datasets;
wherein an ith x coordinate dataset from the first plurality of x coordinate datasets represents a location of an ith first pupil centroid;
wherein i is greater than or equal to 1 and less than or equal to N;
determining, for each of the fourth plurality of video frames, x and y coordinates for a second eye pupil centroid; and
generating a second plurality of x coordinate datasets;
wherein a jth x coordinate dataset from the second plurality of x coordinate datasets represents a location of a jth second pupilar centroid;
wherein j is greater than or equal to 1 and less than or equal to M.

6. The device of claim 5 wherein said processor and memory are configured to:
graphically display a first curve comprising N x coordinate datasets versus time; and
graphically display a second curve comprising M x coordinate datasets versus time.

7. The device of claim 6 wherein said processor and memory are configured to:
set i=1 and j=1;
subtract the ith x coordinate dataset from the jth x coordinate dataset to form a kth x coordinate dataset, each of the kth x coordinate dataset represents a hth dynamic IPD;
when i is less than N, set i=i+1;
when j is less than M, set j=j+1; and
repeat the setting and the subtracting until at least one of i=N and j=M is true.

8. The device of claim 7 wherein said processor and memory are configured to form a third curve comprising each of the hth dynamic IPD versus time.

9. The device of claim 8 wherein said processor and memory are configured to:
identify a first substantially linear portion of the third curve, the first substantially linear portion comprising a positive slope;
identify a second substantially linear portion of the third curve, the second substantially linear portion comprising a negative slope;
generate a graphical plot of the visual stimulus path, the graphical plot comprising a first linear portion comprising a positive slope and a second linear portion comprising a negative slope;
overlap the third curve onto the graphical plot of the visual stimulus path; and
adjust the third curve to fit onto graphical plot of the visual stimulus path.

10. The device of claim 1 wherein said processor and memory are configured to compare the dynamic IPDs with the visual stimulus path by performing at least:
optimizing a graph of the dynamic IPDs with at least one parameter; and
merging the optimized graph of the dynamic IPDs with the visual stimulus path.

11. A non-transitory computer-readable medium having computer-executable instructions for causing a computing device comprising a processor and associated memory to perform a method for screening a person for convergence insufficiency (CI), the method comprising:
recording, with a first image sensor, movement of a first eye of the person;
recording, with a second image sensor, movement of a second eye of the person;
displaying on a display a first visual stimulus and a second visual stimulus;
causing, in alternating fashion, convergent movement and divergent movement in the first visual stimulus and the second visual stimulus along a visual stimulus path;
recording with the first image sensor, dynamic movement of the first eye along the visual stimulus path;
recording with the second image sensor, dynamic movement of the second eye along the visual stimulus path;
determining respective centroid positions of the second eye and the first eye during the convergent and divergent movement of the first visual stimulus and the second visual stimulus based on the recorded dynamic movements of the first eye and the second eye; and
calculating from the respective centroid positions a plurality of interpupillary distances (IPDs) over time, and from the plurality of the IPDs, generating dynamic IPDs over time, and
comparing the dynamic IPDs with the visual stimulus path to serve as an indicator for whether the person has CI.

12. The non-transitory computer-readable medium of claim 11 wherein a duration of each of the convergent movement and the divergent movement is 80-100 seconds.

13. The non-transitory computer-readable medium of claim 11 wherein the method comprises:
using a first infrared (IR) source configured to irradiate the first eye and a second IR source configured to irradiate second eye; and
generating a first plurality of video frames showing movement of the first eye, and generating a second plurality of video frames showing movement of the second eye.

14. The non-transitory computer-readable medium of claim 13 wherein the method comprises:
identifying second blink pixels comprising second eye blinks in the second plurality of video frames;
forming a third plurality of video frames by removing the second blink pixels from the second plurality of video frames;
identifying first blink pixels comprising first eye blinks in the first plurality of video frames; and
forming a fourth plurality of video frames by removing the first blink pixels from the first plurality of video frames.

15. The non-transitory computer-readable medium of claim 13 wherein the generating of the first plurality of video frames comprises:
filtering each of the first plurality of video frames using a pixel intensity threshold to form a third plurality of video frames, each of the third plurality of video frames comprising a black background in combination with a white background, a first eye image, the third plurality of video frames comprising an N number of video frames;
filtering each of the second plurality of video frames using the pixel intensity threshold to form a fourth plurality of video frames, each of the fourth plurality of video frames comprising a black background in combination with a white background, a second eye image, the fourth plurality of video frames comprising an M number of video frames;
determining, for each of the third plurality of video frames, x and y coordinates for a first eye pupil centroid; and
generating a first plurality of x coordinate datasets;
wherein an ith x coordinate dataset from the first plurality of x coordinate datasets represents a location of an ith first pupil centroid;
wherein i is greater than or equal to 1 and less than or equal to N;
determining, for each of the fourth plurality of video frames, x and y coordinates for a second eye pupil centroid; and
generating a second plurality of x coordinate datasets;
wherein a jth x coordinate dataset from the second plurality of x coordinate datasets represents a location of a jth second pupilar centroid;
wherein j is greater than or equal to 1 and less than or equal to M.

16. The non-transitory computer-readable medium of claim 15 wherein the method comprises:
graphically displaying a first curve comprising N x coordinate datasets versus time; and
graphically displaying a second curve comprising M x coordinate datasets versus time.

17. The non-transitory computer-readable medium of claim 16 wherein the method comprises:
setting i=1 and j=1;
subtracting the ith x coordinate dataset from the jth x coordinate dataset to form a kth x coordinate dataset, each of the kth x coordinate dataset represents a hth dynamic IPD;
when i is less than N, setting i=i+1;
when j is less than M, setting j=j+1; and
repeating the setting and the subtracting until at least one of i=N and j=M is true.

18. The non-transitory computer-readable medium of claim 17 wherein the method comprises forming a third curve comprising each of the hth dynamic IPD versus time.

19. The non-transitory computer-readable medium of claim 18 wherein the method comprises:
identifying a first substantially linear portion of the third curve, the first substantially linear portion comprising a positive slope;
identifying a second substantially linear portion of the third curve, the second substantially linear portion comprising a negative slope;
generating a graphical plot of the visual stimulus path, the graphical plot comprising a first linear portion comprising a positive slope and a second linear portion comprising a negative slope;
overlapping the third curve onto the graphical plot of the visual stimulus path; and
adjusting the third curve to fit onto graphical plot of the visual stimulus path.

20. The non-transitory computer-readable medium of claim 11 wherein the comparing of the dynamic IPDs with the visual stimulus path comprises:
optimizing a graph of the dynamic IPDs with at least one parameter; and
merging the optimized graph of the dynamic IPDs with the visual stimulus path.

* * * * *